US007041280B2

(12) United States Patent
Holmes-Farley et al.

(10) Patent No.: US 7,041,280 B2
(45) Date of Patent: May 9, 2006

(54) ARYL BORONATE FUNCTIONALIZED POLYMERS FOR TREATING OBESITY

(75) Inventors: Stephen Randall Holmes-Farley, Arlington, MA (US); W. Harry Mandeville, III, Lynnfield, MA (US); Pradeep K. Dhal, Westford, MA (US); Chad Cori Huval, Somerville, MA (US); Xinhua Li, Newton, MA (US); Steven Craig Polomoscanik, Bedford, MA (US)

(73) Assignee: Genzyme Corporation, Cambridge, MA (US)

( * ) Notice: Subject to any disclaimer, the term of this patent is extended or adjusted under 35 U.S.C. 154(b) by 317 days.

(21) Appl. No.: 10/187,316

(22) Filed: Jun. 27, 2002

(65) Prior Publication Data

US 2003/0059399 A1    Mar. 27, 2003

Related U.S. Application Data

(60) Provisional application No. 60/359,473, filed on Feb. 22, 2002, provisional application No. 60/302,221, filed on Jun. 29, 2001.

(51) Int. Cl.
*A61K 31/80* (2006.01)

(52) U.S. Cl. ............... 424/78.17; 424/78.18; 424/78.26; 525/337; 528/4; 528/8; 528/394

(58) Field of Classification Search .......... 528/4, 528/8, 394; 525/337
See application file for complete search history.

(56) References Cited

U.S. PATENT DOCUMENTS

| | | | |
|---|---|---|---|
| 4,496,722 A | 1/1985 | Gallop et al. | |
| 4,634,722 A * | 1/1987 | Gallop ........................ | 523/106 |
| 5,290,817 A | 3/1994 | Petraitis | |
| 5,356,893 A | 10/1994 | Bradshaw et al. | |
| 5,472,628 A | 12/1995 | Panandiker et al. | |
| 5,487,888 A | 1/1996 | Mandeville, III et al. | |
| 5,496,545 A | 3/1996 | Holmes-Farley et al. | |
| 5,607,669 A | 3/1997 | Mandeville, III et al. | |
| 5,618,530 A | 4/1997 | Mandeville, III et al. | |
| 5,624,963 A | 4/1997 | Mandeville, III et al. | |
| 5,631,371 A | 5/1997 | Bloczynski | |
| 5,667,775 A | 9/1997 | Holmes-Farley et al. | |
| 5,679,717 A | 10/1997 | Mandeville, III et al. | |
| 5,693,675 A | 12/1997 | Mandeville, III et al. | |
| 5,702,696 A | 12/1997 | Mandeville, III et al. | |
| 5,702,952 A | 12/1997 | Sundrehagen et al. | |
| 5,703,188 A | 12/1997 | Mandeville, III et al. | |
| 5,726,343 A | 3/1998 | Ziegler et al. | |
| 5,739,318 A | 4/1998 | Frantzen et al. | |
| 5,840,677 A | 11/1998 | Nielsen et al. | |
| 5,866,568 A | 2/1999 | Bradbury et al. | |
| 5,900,475 A | 5/1999 | Mandeville, III et al. | |
| 5,925,379 A | 7/1999 | Mandeville, III et al. | |
| 5,972,873 A | 10/1999 | Nielsen et al. | |
| 5,985,938 A | 11/1999 | Holmes-Farley et al. | |
| 6,034,129 A | 3/2000 | Mandeville, III et al. | |
| 6,083,495 A | 7/2000 | Holmes-Farley et al. | |
| 6,083,497 A | 7/2000 | Huval et al. | |
| 6,184,363 B1 | 2/2001 | Shoichet et al. | |
| 6,197,967 B1 | 3/2001 | Vollmueller et al. | |
| 6,203,785 B1 | 3/2001 | Holmes-Farley et al. | |
| 6,264,937 B1 | 7/2001 | Mandeville, III et al. | |
| 6,299,868 B1 | 10/2001 | Jozefiak et al. | |

FOREIGN PATENT DOCUMENTS

| | | |
|---|---|---|
| DE | 3930663 C1 | 11/1990 |
| DE | 4307243 A1 | 10/1993 |
| EP | 0 354 434 A2 | 2/1990 |
| EP | 0 478 050 A1 | 4/1992 |
| EP | 0 495 627 A1 | 7/1992 |
| EP | 0 571 928 A1 | 12/1993 |
| EP | 1 072 597 A1 | 1/2001 |
| GB | 2 276 162 A | 9/1994 |
| JP | 2000-336045 | 12/2000 |

(Continued)

OTHER PUBLICATIONS

Hansch C. et al. "Hammett Sigmas" in Exploring QSAR Hydrophobic, Electronic and Steric Constants, *American Chemical Society*: Washington, D.C. pp. 219-304 (1995).

(Continued)

*Primary Examiner*—Marc S. Zimmer
(74) *Attorney, Agent, or Firm*—Fish & Neave IP Group Ropes & Gray, LLP

(57) ABSTRACT

Disclosed are polymers comprising one or more phenyl boronate ester, boronamide or boronate thioester groups. The phenyl boronate ester, boronamide and boronate thioester groups are represented by one of the following structural formulas:

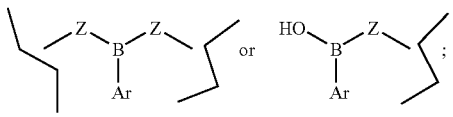

Ar in Structural Formulas (I) and (II) is substituted or unsubstituted; and each Z is —O—, —NH— or —S— and is independently selected. Pharmaceutically acceptable salts of the polymer are also included. The aryl boronate ester, boronamide or boronate thioester can be cleaved to release the corresponding aryl boronic acid.

Also disclosed are pharmaceutical compositions comprising the polymers of the present invention and a pharmaceutically acceptable carrier or diluent; and methods of treating a subject for obesity with the polymers of the present invention.

117 Claims, 10 Drawing Sheets

FOREIGN PATENT DOCUMENTS

| | | |
|---|---|---|
| WO | WO 92/08722 A1 | 5/1992 |
| WO | WO 94/14803 A1 | 7/1994 |
| WO | WO 95/01326 A1 | 1/1995 |
| WO | WO 95/11243 A1 | 4/1995 |
| WO | WO 95/20569 A1 | 8/1995 |
| WO | WO 96/02288 A1 | 2/1996 |
| WO | WO 96/17833 A1 | 6/1996 |
| WO | WO 96/21716 A1 | 7/1996 |
| WO | WO 96/30333 A1 | 10/1996 |
| WO | WO 96/40681 A1 | 12/1996 |
| WO | WO 97/30055 A1 | 8/1997 |
| WO | WO 98/22820 A1 | 5/1998 |
| WO | WO 98/47885 A1 | 10/1998 |
| WO | WO 98/56392 A1 | 12/1998 |
| WO | WO 99/05107 A1 | 2/1999 |
| WO | WO 99/23073 A1 | 5/1999 |
| WO | WO 99/47474 A1 | 9/1999 |
| WO | WO 00/06537 A1 | 2/2000 |
| WO | WO 00/14083 A1 | 3/2000 |
| WO | WO 00/27394 A1 | 5/2000 |
| WO | WO 00/27820 A1 | 5/2000 |
| WO | WO 00/35904 A1 | 6/2000 |
| WO | WO 00/42213 A1 | 7/2000 |
| WO | WO 00/61571 A1 | 10/2000 |
| WO | WO 01/16108 A2 | 3/2001 |

OTHER PUBLICATIONS

Kinder, D. H. et al., "Synthesis of 2-Amino-3-Boronopropionic Acid: A Boron-Containing Analog of Aspartic Acid" *J. Org. Chem.*, 52(12): 2452-2454 (1987).

Matteson, D. S., et al., "Directed Chiral Synthesis with Pinanediol Boronic Esters", *J. Am. Chem. Soc.*, 102(25): 7590-7591 (1980).

Ishiyama, T., et al., "Palladium(0)-Catalyzed Cross-Coupling Reaction of Alkoxydiboron with Haloarenes: A Direct Procedure for Arylboronic Esters", *J. Org. Chem.*, 60(23): 7508-7510 (1995).

Folch, J. et al., "A Simple Method For The Isolation and Purification of Total Lipides From Animal Tissues", *J. Biol. Chem.*, 226: 497-509 (1957).

Hall, I. H. et al., "Hypolipidemic, Anti-Obesity, Anti-inflammatory, Anti-osteoporotic, and Anti-neoplastic Properties of Amine Carboxyboranes", *Environ. Health Perspect.* 102(S3): 21-30 (1994).

Hall, D.G., et al., "N, N-Diethanolaminomethyl Polystyrene: An Efficient Solid Suport to Immobilze Boronic Acids", *Angew. Chem. Int. Ed.*, 38(20): 3064-3067 (1999).

Gravel, M. et al,. "Universal Solid-Phase Approach for the Immobilization, Derivatization, and Resin-to-Resin Transfer Reactions of Boronic Acids", *J. Org. Chem.*, 67: 3-15 (2002).

Draffin, S.P., et al., "Highly Fructose Selective Transport Promoted by Boronic Acids Based on a Pentaerythritol Core," *Organic Letters*, 3(6): 917-920 (2001).

Reuman, M. et al., "Synthesis and Antibacterial Activity of Some Novel 1-Substituted 1, 4-Dihydro-4-Oxo-7-pyridinyl-3-quinolinecarboxylic acids. Potent Antistaphylococcal Agents." *J. Med. Chem.*, 38(14): 2531-2540 (1995).

Sakai, M. et al., "Rhodium-Catalyzed Addition of Organoboronic Acids to Aldehydes", *Angew. Chem. Int. Ed.* 37(23): 3279-3281 (1998).

Barba, V. et al., "Synthesis and Molecular Structures of Dimeric Boron Compounds", *J. Organometallic Chem.*, 604: 273-282 (2000).

Saito, S. et al., "Synthesis of Biaryls via a Nickel(0)-Catalyzed Cross-Coupling Reaction of Chloroarenes with Arylboronic Acids", *J. Org. Chem.* 62: 8024-8030 (1997).

Kobayashi, Y. et al., "Preparation of Functionalized Zinc Borates and their Coupling Reaction with Allylic Acetates", *Tetrahedron Lett.* 39: 7537-7540 (1998).

Aoki, T., et al., "Endothelial cell differentiation into capillary structures by copolymer surfaces with phenylboronic acid groups," *J Biomater Sci: Polymer Edn.*, 7(7) :539-550, (1995).

Miyazaki, H., et al., "Boronate-Containing Polymer as Novel Mitogen for Lymphocytes," *Biochemical and Biophysical Research Communications*, 195(2) ;829-836, (1993).

* cited by examiner

ARYL BORONATE FUNCTIONALIZED POLYMERS FOR TREATING OBESITY

RELATED APPLICATIONS

This application claims the benefit of U.S. Provisional Application No. 60/302,221, filed Jun. 29, 2001, and U.S. Provisional Application No. 60/359,473, filed Feb. 22, 2002, the entire teachings of which are incorporated herein by reference.

BACKGROUND OF THE INVENTION

Human obesity is a recognized health problem with approximately ninety-seven million people considered clinically overweight in the United States. Various chemical approaches have been used for treating obesity. In one such approach, a medicament which inhibits lipases is administered to the obese patient. Lipases are key enzymes in the digestive system which break down diglycerides and triglycerides into monoglycerides and fatty acids. Diglycerides and triglycerides have a high caloric content but are not absorbed by the small intestine until broken down by the lipases. Therefore, inhibition of lipases within the digestive system results in a reduction in the absorption of fat and consequently a decrease in caloric uptake. XENICAL is an example of a commercially available lipase inhibitor that is used for treating obesity.

Administration of lipase inhibitors results in stools with a high fat or oil content from the undigested diglycerides and triglycerides. Leakage of oil from the stool is an unpleasant side effect that often occurs when stools have a high fat or oil content. This condition is referred to as "oily stool" or "leaky stool". It has been reported in U.S. application Ser. No. 09/166,453 that fat-binding polymers, when co-administered with lipase inhibitors, can bind with or "stabilize" the oil and thereby reduce or eliminate the leakage of oil from the stool. However, the need to administer two drugs can reduce patient compliance because it is burdensome and inconvenient. The development of new drugs which both inhibit lipases and bind the lipids which cause "leaky stools" would be an advance with respect to managing and treating obesity in patients.

SUMMARY OF THE INVENTION

It has now been found that polymers with aryl boronate ester, boronamide and boronate thioester groups that can be hydrolyzed to liberate aryl boronic acids inhibit lipases in vivo (see Example 14). It is expected that mammals which have been administered fat binding polymers with these cleavable aryl boronate ester, boronamide and boronate thioester groups will have reduced levels of the "leaky stool" side effect compared with other lipase inhibiting compounds. Based on this discovery, novel polymers, including fat-binding polymers, with cleavable aryl boronate ester, boronamide and/or boronate thioester groups and the use of such polymers for treating obesity are disclosed herein.

One embodiment of the present invention is a polymer comprising one or more aryl boronate ester, boronamide and/or boronate thioester groups represented by Ar—B-(Z-)$_2$ or Ar—B-(ZH)(Z-), wherein each Z is —O—, —NH— or —S— and is independently selected. Preferably, each Z is —O—. The aryl boronate ester, boronamide or boronate thioester can be cleaved or hydrolyzed to release the corresponding aryl boronic acid. The aryl group represented by Ar is substituted or unsubstituted. Preferably, the aryl boronic ester groups are phenyl boronic esters represented Structural Formulas (I) or (II):

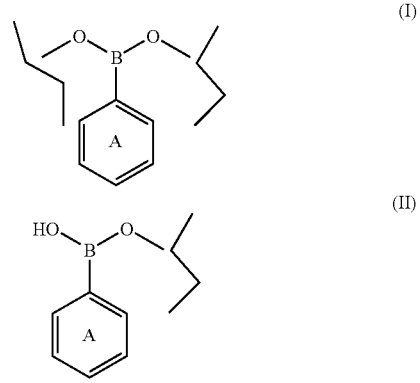

Phenyl Ring A in Structural Formulas (I) and (II) is substituted or unsubstituted.

Another embodiment of the present invention is a pharmaceutical composition. The pharmaceutical composition comprises the polymer described above and a pharmaceutically acceptable carrier or diluent.

Another embodiment of the present invention is a method for removing fat from the gastrointestinal tract (or inhibiting uptake of fat in the gastrointestinal tract) of a subject in need of such treatment (e.g., treating a subject for obesity). The method comprises the step of administering an effective amount of the polymer described above to the subject.

The polymers disclosed herein are believed to release aryl boronic acids in the gastrointestinal tract. Aryl boronic acids are potent inhibitors of lipase enzymes. The polymers of the present invention are therefore effective in removing fat from the gastrointestinal tract of subjects for whom reduced fat absorbtion can be clinically beneficial. Thus, these polymers are useful in the treatment of obesity. Because many of the disclosed polymers bind the lipids, the unpleasant leakage of oil from the stools that often accompanies the administration of lipase inhibitors is reduced or eliminated compared with other lipase inhibiting drugs. The disclosed polymer drugs and many of the liberated boronic acid groups are largely unabsorbed by the intestines and therefore also have the advantage of causing minimal systemic side effects.

DETAILED DESCRIPTION OF THE INVENTION

Figure 1:
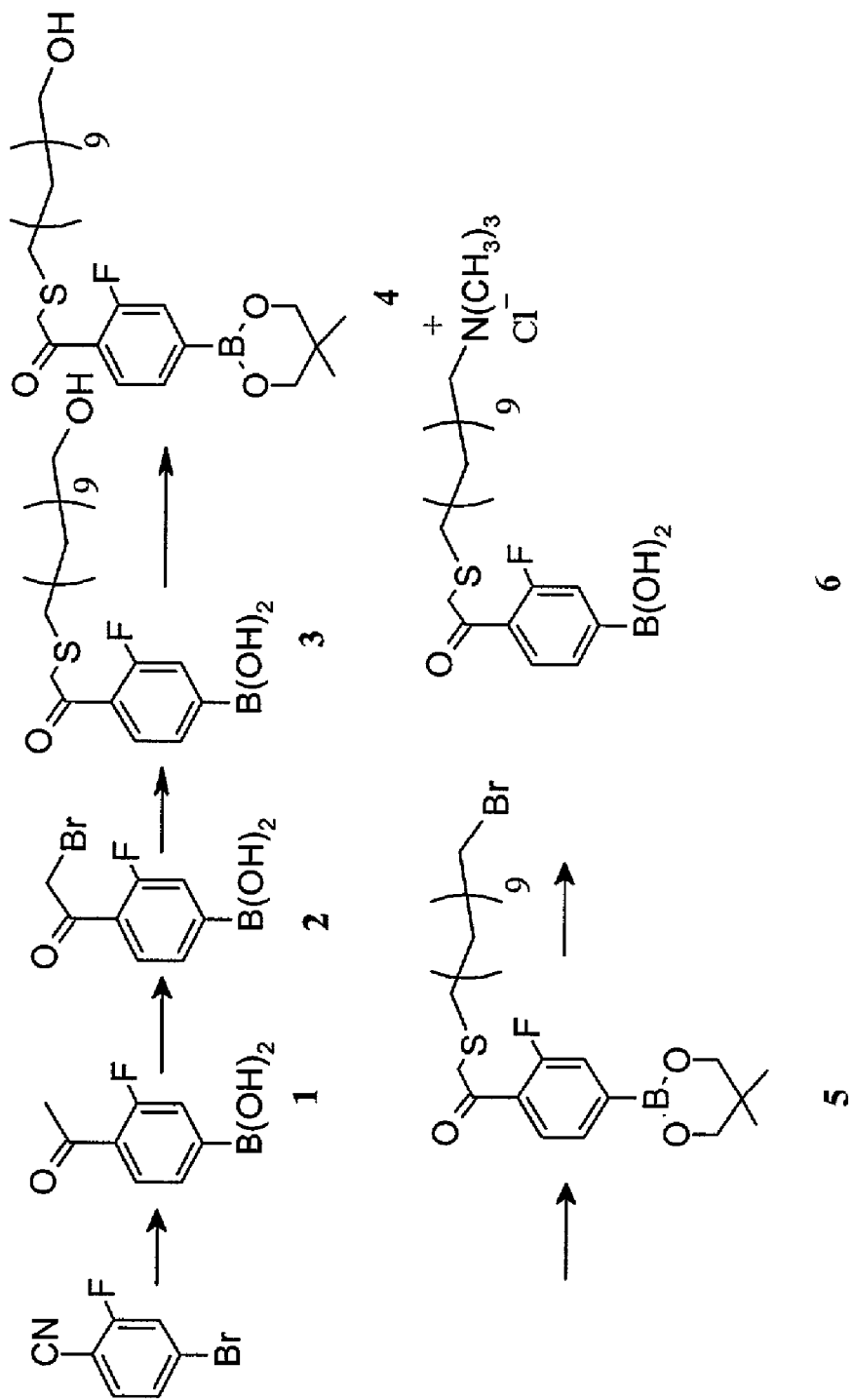
FIG. 1 is a schematic showing the synthesis of 4-(14'-trimethylammonium-3'-thia-1'-ketotetradecyl)-3-fluorophenylboronic acid chloride (6).

The polymers of the present invention comprise one or more cleavable aryl boronate ester, boronamide or boronate thioester groups. The invention is described below with respect to aryl boronate esters, i.e., wherein each Z is —O—. It is to be understood that these descriptions apply to the corresponding boronamides and boronate thioesters, i.e., wherein one or both Zs are —NH— or —S—.

These polymers bind lipids in the gastrointestinal tract and also inhibit the action of lipase enzymes. "Cleavable" means that the corresponding aryl boronic acid group is released from the polymer when the aryl boronate ester is hydrolyzed. Thus, the polymers of the present invention are limited to polymers in which the boronate ester group is "between" Ar (or Phenyl Ring A) and the polymer backbone and that the only covalent linkage between the Ar (or Phenyl Ring A) and the remainder of the polymer is through the boronate ester bond(s). Although Applicants do not wish to be bound by any particular mechanism, it is believed that the boronate ester functional group is hydrolyzed in vivo, thereby liberating an aryl boronic acid, which then acts to inhibit the lipase.

Ar and Phenyl Ring A in Structural Formulas (I) or (II) are substituted or unsubstituted. Ar and Phenyl Ring A are "substituted" when Ar comprises at least one substituent and Phenyl Ring A comprises at least one substituent other than the boronate ester group. Suitable substituents are as described below for aryl groups. Preferably, Ar and Phenyl Ring A are substituted with at least one electron withdrawing group.

An electron withdrawing group is a substituent which results in a phenyl ring that has less electron density when the group is present than when it is absent. Electron withdrawing groups have a Hammet sigma value greater than one (see, for example, C. Hansch, A. Leo and D. Hoeckman, "Exploring QSAR Hydrophobic, Electronic and Steric Constants", American Chemical Society (1995), pages 217–32) Examples of electron withdrawing groups include halogens, —$NO_2$, —CN and —X—R. X is —CHD—, —$CD_2$—, —COO—, —CONH—, —CO— or —$SO_2$—; D is a halogen; and R is a substituted or unsubstituted straight chained hydrocarbyl group with an ether, thioether, phenylene, amine or ammonium linkage. Additional values for X include —S(O)— and —$S(O)_2O$—. In one aspect, the hydrocarbyl group represented by "R" is a straight chained hydrocarbyl group with an ether or thioether linkage and optionally substituted at the terminal position with an amine, halogen, —$CF_3$, thiol, ammonium, alcohol, —COOH, —$S_{O3}H$, —$OSO_3H$ or phosphonium group. In another aspect, the hydrocarbyl group represented by R is a straight chained hydrocarbyl group with an ammonium linkage and optionally substituted at the terminal position with an amine, halogen, —$CF_3$, thiol, ammonium group, alcohol, —COOH, —$SO_3H$, —$OSO_3H$ or phosphonium group. In yet another aspect, the hydrocarbyl group represented by R is a straight chained hydrocarbyl group substituted at the terminal position with an amine, halogen, —$CF_3$, thiol, ammonium group, alcohol, —COOH, —$SO_3H$, —$OSO_3H$ or phosphonium group.

Alternatively, R is —$CH_2$—O[—$(CH_2)_pO]_m$—$(CH_2)_p$—Y or —$C(O)CH_2$—S[—$(CH_2)_pO]_m$—$(CH_2)_p$—Y, p is 2 or 3, m is an integer from 1–5 and Y is an ammonium group.

A "straight chained hydrocarbyl group" is a polyalkylene group, i.e., —$(CH_2)_x$— where x is a positive integer (e.g., between 1 and about 30), preferably between about 6 and about 30, more preferably between about 6 and about 15. A "linkage group" refers to a functional group which replaces a methylene in a straight chained hydrocarbyl. Examples of suitable linkage groups include an alkene, alkyne, phenylene, ether (—O—), thioether (—S—), amine [—$N^+(R^a)$]— or ammonium [—$N^+(R^aR^b)$—]. $R^a$ and $R^b$ are independently —H, alkyl, substituted alkyl, phenyl, substituted phenyl, or, taken together with the nitrogen atom to which they are bonded, a non-aromatic, nitrogen-containing heterocyclic group. Preferably, $R^a$ and $R^b$ are not —H. More preferably, $R^a$ and $R^b$ are both alkyl groups and even more preferably, both methyl. $R^a$ and $R^b$ can be the same or different, but are preferably the same.

The terms "terminal position" or "terminus" refer to the methylene carbon of the straight chained hydrocarbyl group most distant from Ar, Phenyl Ring A or Phenyl Ring B, as described below. Substituents at the terminal position of a straight chained hydrocarbyl group are referred to herein as "terminal substituents". As noted above, examples of suitable terminal substituents include amine (—$NR^cR^d$), halogen, —$CF_3$, thiol, ammonium (—$N^+R^cR^dR^e$), alcohol (—OH), —COOH, —$SO_3H$, —$OSO_3H$ or phosphonium group. $R^c$, $R^d$ and $R^e$ in an ammonium group are independently —H, alkyl, substituted alkyl, phenyl, substituted phenyl, or, taken together with the nitrogen atom to which they are bonded, a nitrogen-containing, non-aromatic heterocyclic group. Preferably, $R^c$, $R^d$ and $R^e$ are not —H. More preferably, $R^c$, $R^d$ and $R^e$ are all alkyl groups (i.e., a trialkylammonium group) and even more preferably, all methyl (i.e., a trimethylammonium group). $R^c$, $R^d$ and $R^e$ can be the same or different, but are preferably all the same.

In one aspect, the hydrocarbyl group represented by R is substituted at the terminal position with a group —Y, wherein —Y is selected such that YH is a small molecule polyamine. For example, when YH is a small molecule polyamine, —Y can be represented by —[NH—$(CH_2)_q]_r$—$NH_2$). q is an integer from 2 to about 10 and r is an integer from 1 to about 5. Examples of small molecule polyamines include spermine, spermidine, 1,2-diaminoethane, 1,3-diaminopropane or 1,4-diaminobutane. Optionally, one or more of the secondary amine can optionally be N-alkylated or N,N-dialkylated; the primary amine is optionally N-alkylated, N,N-dialkylated or N,N,N-trialkylated.

A "substituted hydrocarbyl group" has one or more substituents bonded at one or more positions other than at the terminus. Suitable substituents are those which do not significantly lower the lipase inhibiting ability or fat binding ability of the polymer, for example, do not lower either activity by more than a factor of about two. Examples of suitable substituents include C1–C3 straight chained or branched alkyl, C1–C3 straight chained or branched haloalkyl, —OH, halogen (—Br, —Cl, —I and —F), —O(C1–C3 straight chain or branched alkyl) or —O(C1–C3 straight chain or branched haloalkyl).

In a preferred embodiment, the polymer of the present invention comprises one more phenyl boronate ester group represented by Structural Formula (III):

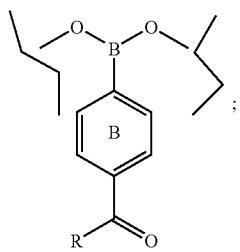
(III)

R is as described above.

Phenyl Ring B is substituted or unsubstituted. Phenyl Ring B is said to be "substituted" when it has one or more substituents other than —CO—R and the boronate ester. Suitable substituents for Phenyl Ring B are as described below for aryl groups. Preferably, Phenyl Ring B is substituted with one or more electron withdrawing groups. Fluorine is a preferred electron withdrawing group for Phenyl Ring B. Examples of suitable substitution patterns for Phenyl Ring B include 3-fluoro and 2,5-difluoro, wherein position 1 is the carbon bonded to boron.

In a more preferred embodiment, the phenyl boronate ester groups in the polymers of the present invention are represented by Structural Formula (IV):

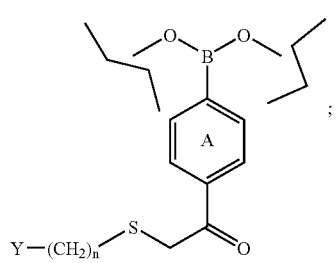
(IV)

In Structural Formula (IV), Y is an ammonium group (preferably trialkylammonium) and more preferably trimethylammonium) and n is an integer from 1 to about 30, preferably from about 3 to about 30 and more preferably from about 6 to about 15.

An arylboronate ester group (or phenyl boronate ester group) comprises an aryl boronate portion (or a phenyl boronate portion) and an "ester portion". The aryl boronate portion (or phenyl boronate portion) can be connected directly or "linked" directly to the polymer by one or two boronate ester bonds, in which case the "ester portion" is the polymer backbone. Examples of polymers of this type include polyvinyl alcohol or a polysaccharide with an aryl boronate group(s) (or phenyl boronate group(s)) bonded directly to the polymer backbone through one or two boronate ester bonds formed between the boronate group and alcohol groups from the polymer backbone. Alternatively, the "ester portion" is a side chain which is pendent from the polymer backbone and serves to link or connect the aryl boronate group (or phenyl boronate group) to the polymer backbone. In this case, the "ester portion" typically comprises at least one and preferably at least two alcohol functionalities which are suitably positioned to form boronate ester bonds with an aryl boronic acid (or a phenyl boronic acid), e.g., an alkyldiol. Structural Formulas (V), (VI) and (VII) each show an example of a phenyl boronate ester formed from an alkyl-1,2-diol, an alkyl-1,3-diol or an alkyl-1,5-diol, respectively, and a phenyl boronic acid:

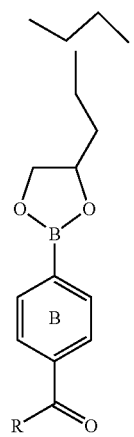
(V)

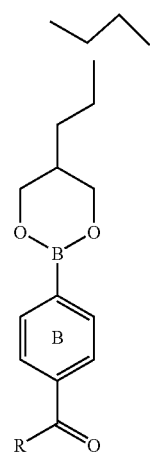
(VI)

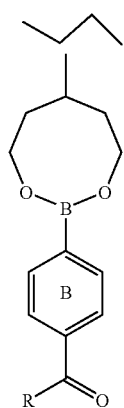
(VII)

Specific examples of monomers with side chains comprising alkyl-1,2-diol groups are shown below:

Specific examples of monomers with side chains comprising alkyl-1,3-diol groups are shown below:

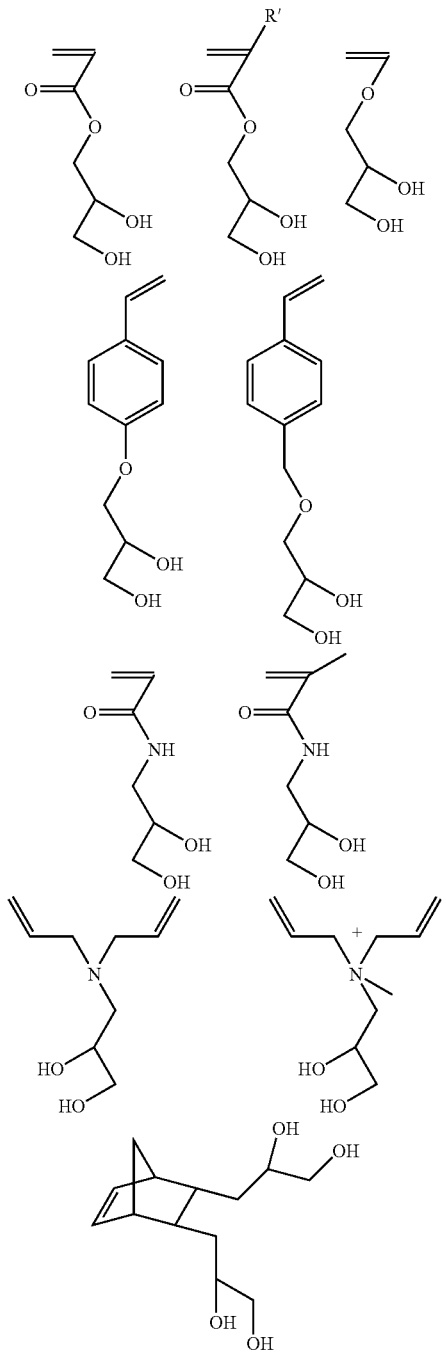

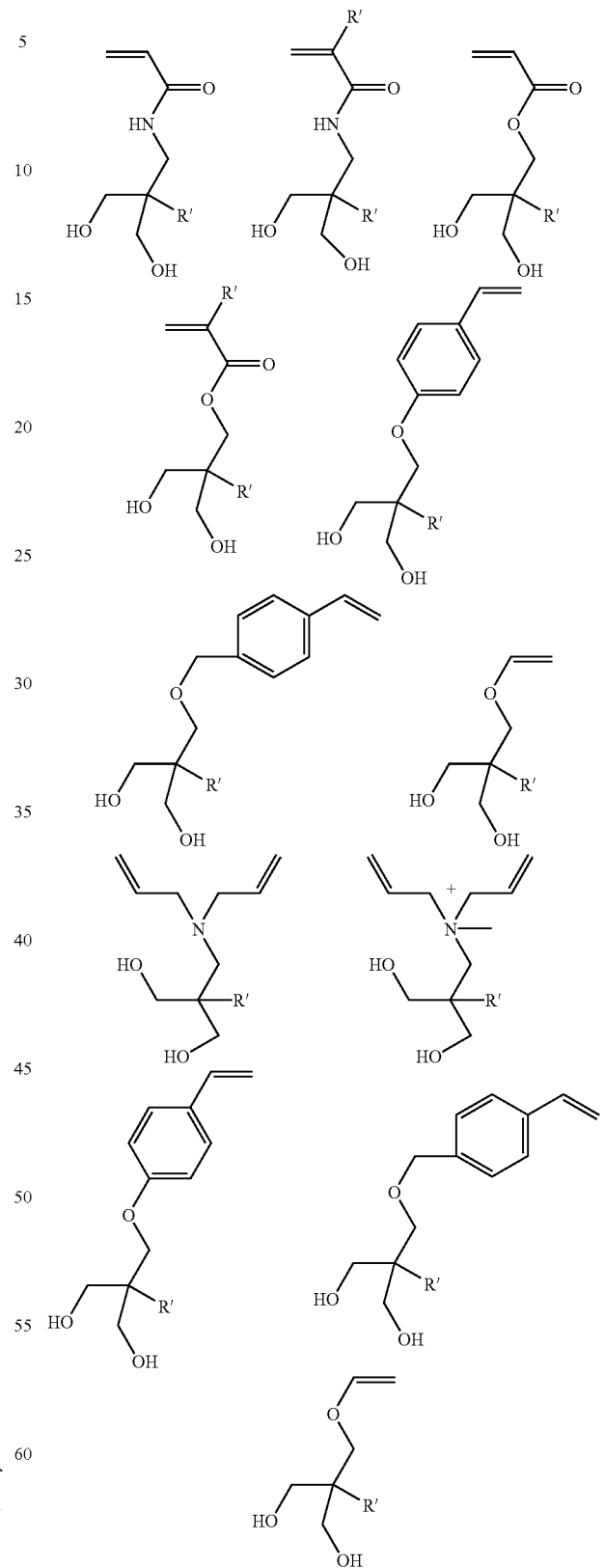

The monomers can be polymerized and the alkyl-1,2-diol groups of the resulting polymer esterified with an aryl boronic acid to form a boron-functionalized polymer of the present invention. Alternatively, the alkyl-1,2-diol groups of the monomers can be esterified with an aryl boronic acid and the resulting boron-functionalized monomer polymerized to form a boron-functionalized polymer of the present invention. Each of the alkyl-1,2-diol functionalized monomers depicted above can be esterified, for example, with any one of the boronic acids shown in FIG. 5.

The above monomers can be polymerized and the alkyl-1, 3-diol groups of the resulting polymer esterified with an aryl boronic acid to form a boron-functionalized polymer of the present invention. Alternatively, the alkyl-1,3-diol groups of the monomers can be esterified with an aryl boronic acid and the resulting boron-functionalized monomer polymerized to form a boron-functionalized polymer of the present invention. Each of the alkyl-1,3-diol containing monomers depicted above can be esterified, for example, with any one of the boronic acids shown in FIG. 5.

Also included in the present invention are polymers comprising phenyl boronamide and/or boronate esters groups corresponding to the structures represented by Structural Formulas (III)–(VII), i.e., wherein one or both boronate oxygen atoms is replaced with —S— and/or —NH—.

Optionally, the polymer side chains comprises a group which increases the ability of the polymer to bind fat, e.g., an amine group or a cationic group such as an ammonium group. Thus, the side chain typically comprises an aminoalkyldiol, i.e., a moiety with one amine and two alcohol groups or the corresponding ammonium group; or a dialkanolamine such as diethanolamine or the corresponding ammonium group. The "corresponding ammonium group" refers to the alkylated or benzylated form of, for example, an aminoalkyldiol or dialkanolamine. Examples include a phenyl boronate esters shown below in Structural Formulas (VIII)–(XI), which are formed from an aminoalkyl-1,2-diol, ammoniumalkyl-1,2-diol, a diethanolamine and diethanolammonium group and a phenyl boronic acid:

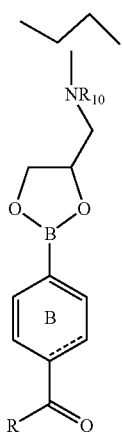

(VIII)

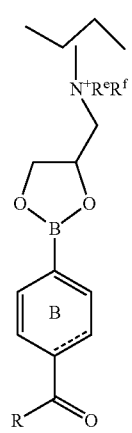

(IX)

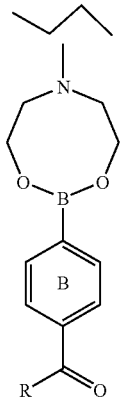

(X)

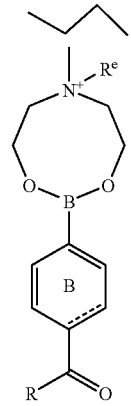

(XI)

$R_{10}$ is —H, a substituted or unsubstituted alkyl group or a substituted or unsubstituted benzyl group, preferably —H. $R^e$ and $R^f$ are independently —H, a substituted or unsubstituted alkyl group or a substituted or unsubstituted benzyl group, preferably —H.

Specific examples of monomers and polymers with side chains comprising diethanol amine groups are shown below:

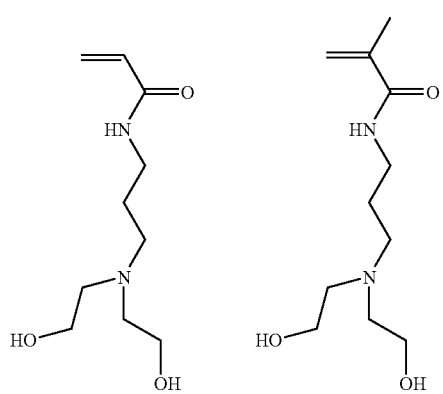

-continued
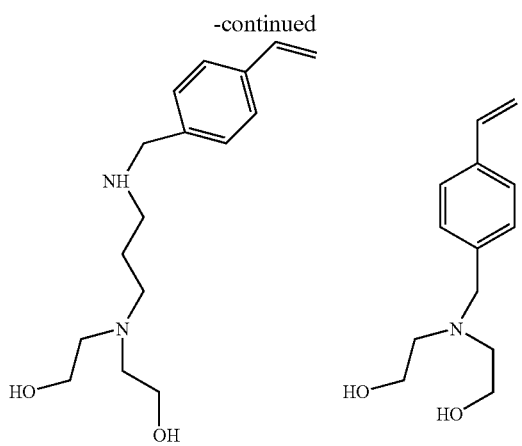
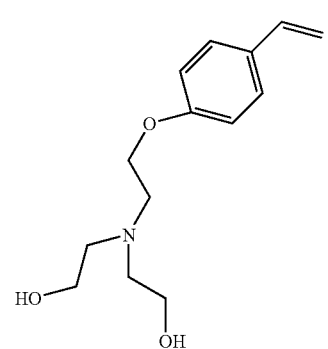
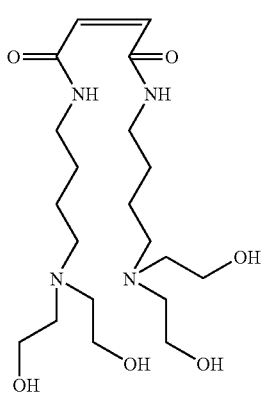
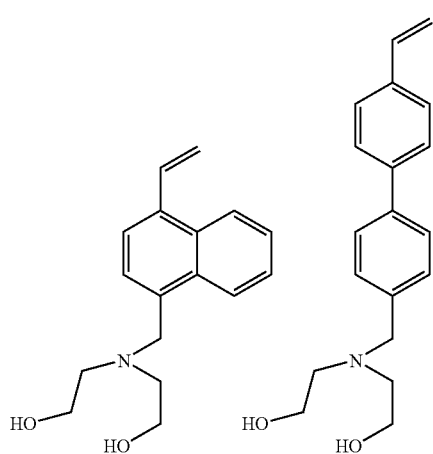
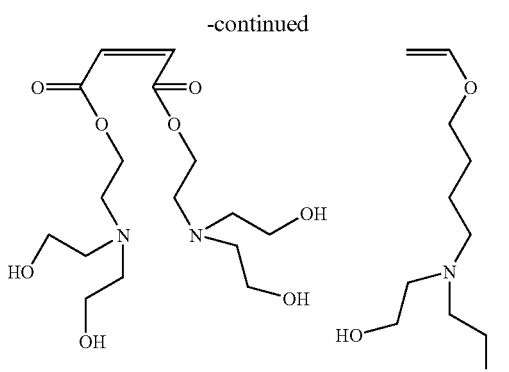
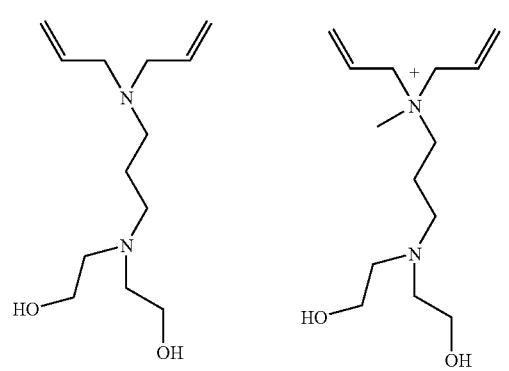
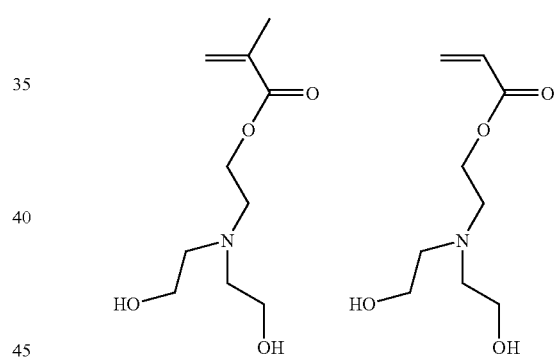
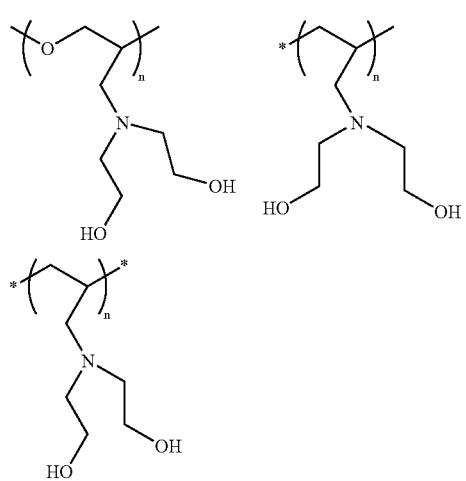

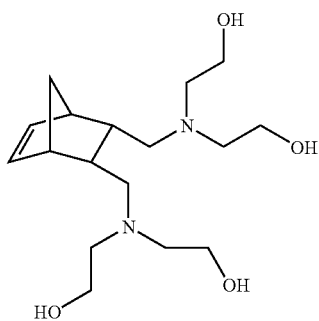

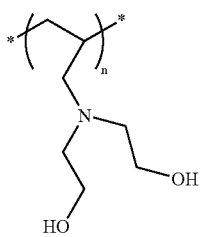

The monomers shown above can be polymerized and the diethanolamine groups of the resulting polymer esterified with an aryl boronic acid to form a boron-functionalized polymer of the present invention. Alternatively, the diethanolamine groups of the monomers can be esterified with an aryl boronic acid and the resulting boron-functionalized monomer polymerized to form a boron-functionalized polymer of the present invention. Each of the diethanolamine-containing monomers depicted above can be esterified, for example, with any one of the boronic acids shown in FIG. 5.

In yet another aspect, side chains of the polymer are polyols with four or more alcohol groups which can form boronate esters. Typically, a boronate ester is formed from two diols in the side chain and the boronic acid. The side chain can comprise more than one aryl boronate ester. Examples of suitable monomers with polyol side chains are shown below:

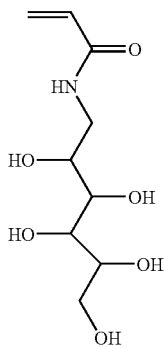 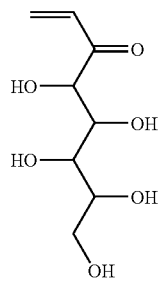

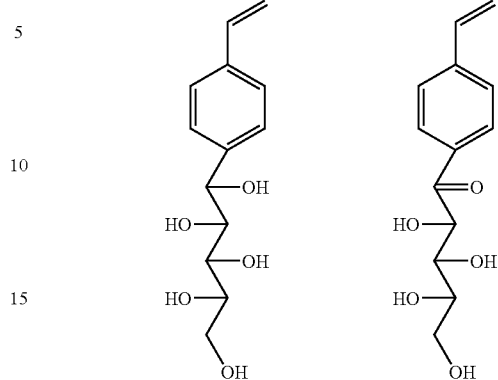

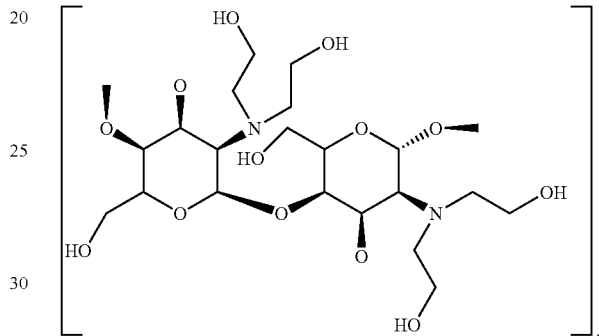

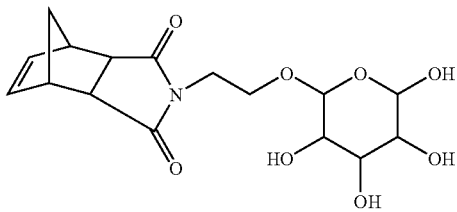

The monomers shown above can be polymerized and the polyols of the resulting polymer esterified with an aryl boronic acid to form a boron-functionalized polymer of the present invention. Alternatively, the polyols of the monomers can be esterified with an aryl boronic acid and the resulting boron-functionalized monomer polymerized to form a boron-functionalized polymer of the present invention. Each of the polyol-containing monomers shown above can be esterified, for example, with any one of the boronic acids shown in FIG. 5.

R and Phenyl Ring B in Structural Formulas (V)–(XI) are as described above. R' in the structures shown above is —H or an alkyl group.

Structural Formula (XII) shows a preferred example of a phenyl boronate ester formed from a phenyl boronic acid and an alkyldiol moiety; Structural Formula (XIII) shows a preferred example of a phenyl boronate ester formed from a phenyl boronic acid and diethanol amine moiety; and Structural Formula (XIV) shows a preferred example of a phenyl boronate ester formed from a phenyl boronic acid and a diethanolammonium moiety:

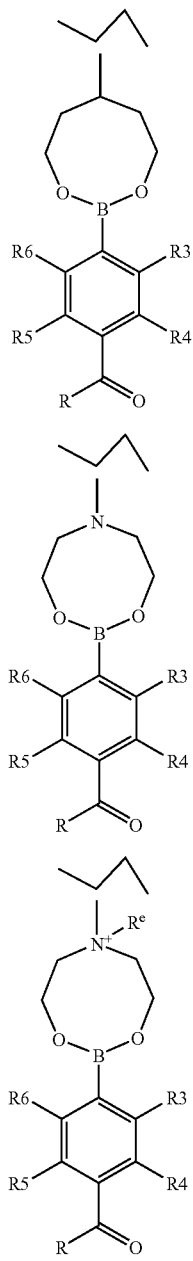

$R_3$–$R_6$ are independently —H or —F; R and $R^e$ are as described above. Preferably, R is —CH$_2$S—(CH$_2$)$_n$Y, wherein Y and n are as described above. In preferred examples, $R_3$ and $R_5$ are —F and $R_4$ and $R_6$ are —H; and $R_3$, $R_5$ and $R_6$ are —H and $R_4$ is —F.

The present invention also includes polymers comprising one or more phenyl boronate ester group(s) formed from a phenyl boronic acid and an alkyldiol, a diethanolamine, or an aminoalkydiol group, e.g., a polymer comprising one or more groups represented by Structural Formula (V)–(XIV).

The term "monomer" refers to both (a) a single molecule comprising one or more polymerizable functional groups prior to polymerization, or (b) a repeat unit of a polymer. An unpolymerized monomer capable of addition polymerization, can, for example, comprise an olefinic bond which is lost upon polymerization. A "boronate functionalized monomer" is a monomer with a boronate ester group in the side chain that release the corresponding boronic acid when the ester is hydrolyzed. A "boronate functionalized polymer" is a polymer with or formed from boronate functionalized monomers that releases the corresponding boronic acid when the ester is hydrolyzed.

In a more preferred embodiment, the present invention is a polymer comprising boronate functionalized monomers represented by Structural Formula (XV):

M is a covalent bond, —CH$_2$—, 1,3-phenylene, 1,4-phenylene, —C(O)O—, —C(O)NR$_1$, —C(O)—, —O—, —NR$_1$—, —CH$_2$NR$_1$— or —CH$_2$O—. Preferably, M is —C(O)NH. Other possible values of M include —N$^+$(R$_1$R$_1$)— and —CH$_2$N$^+$(R$_1$R$_1$)—.

Q is a covalent bond or an inert spacer group. A spacer group serves to separate the phenyl boronate ester from the polymer. A spacer group is "inert" when it contains no functionality that substantially interferes with the fat binding ability of the polymer. Inert spacer groups are preferably hydrocarbyl groups optionally containing one or more linkage groups and is preferably an alkylene group, preferably C1–C30, more preferably C1 to C15 and even more preferably C1–C8. Typically, inert spacer groups are hydrophobic.

R$_1$ is —H, an aliphatic group or a substituted aliphatic group.

R$_2$ is —H or a C1–C6 alkyl group.

W is a group comprising a phenyl boronate ester formed from a phenyl boronic acid and an diethanolamine, an alkyldiol or an aminoalkyldiol group, e.g., a group represented by a Structural Formula selected from (V)–(XIV).

In specific examples of boronate functionalized monomers represented by Structural Formula (XV), -MQW comprises a boronate ester formed from —C(O)NH—(CH$_2$)$_2$—N—(CH$_2$CH$_2$OH)$_2$, —C(O)NH—(CH$_2$)$_3$—N—(CH$_2$CH$_2$OH)$_2$, —C(O)NH—(CH$_2$)$_4$—N—(CH$_2$CH$_2$OH)$_2$, —C(O)O—(CH$_2$)$_2$—N—(CH$_2$CH$_2$OH)$_2$, —C(O)O—(CH$_2$)$_3$—N—(CH$_2$CH$_2$OH)$_2$, —C(O)O—(CH$_2$)$_4$—N—(CH$_2$CH$_2$OH)$_2$, —NH—(CH$_2$)$_2$—N—(CH$_2$CH$_2$OH)$_2$, —NH—(CH$_2$)$_3$—N—(CH$_2$CH$_2$OH)$_2$, —NH—(CH$_2$)$_4$—N—(CH$_2$CH$_2$OH)$_2$, —O—(CH$_2$)$_2$—N—(CH$_2$CH$_2$OH)$_2$, —O—(CH$_2$)$_3$—N—(CH$_2$CH$_2$OH)$_2$, —O—(CH$_2$)$_4$—N—(CH$_2$CH$_2$OH)$_2$, —CH$_2$NH—(CH$_2$)$_2$—N—(CH$_2$CH$_2$OH)$_2$, —CH$_2$NH—(CH$_2$)$_3$—N—(CH$_2$CH$_2$OH)$_2$, —CH$_2$NH—(CH$_2$)$_4$—N—(CH$_2$CH$_2$OH)$_2$, —CH$_2$CH$_2$NH—(CH$_2$)$_2$—N—(CH$_2$CH$_2$OH)$_2$, —CH$_2$CH$_2$NH—(CH$_2$)$_3$—N—(CH$_2$CH$_2$OH)$_2$, —CH$_2$CH$_2$NH—(CH$_2$)$_4$—N—(CH$_2$CH$_2$OH)$_2$, -(1,4-phenylene)CH$_2$NH—(CH$_2$)$_2$—N—(CH$_2$CH$_2$OH)$_2$, -(1,4-phenylene)CH$_2$NH—(CH$_2$)$_3$—N—(CH$_2$CH$_2$OH)$_2$, -(1,4-phenylene)CH$_2$NH—(CH$_2$)$_4$—N—(CH$_2$CH$_2$OH)$_2$, -(1,4-phenylene)NH—(CH$_2$)$_2$—N—(CH$_2$CH$_2$OH)$_2$, -(1,4-phenylene)NH—(CH$_2$)$_3$—N—(CH$_2$CH$_2$OH)$_2$, -(1,4-phenylene)NH—(CH$_2$)$_4$—N—(CH$_2$CH$_2$OH)$_2$, -(1,4-phenylene)O—(CH$_2$)$_2$—N—

(CH₂CH₂OH)₂, -(1,4-phenylene)O—(CH₂)₃—N—(CH₂CH₂OH)₂, -(1,4-phenylene)O—(CH₂)₄—N—(CH₂CH₂OH)₂, —C(O)NH—(CH₂)₂—N⁺(CH₃)—(CH₂CH₂OH)₂, —C(O)NH—(CH₂)₃—N⁺(CH₃)—(CH₂CH₂OH)₂, —C(O)NH—(CH₂)₄—N⁺(CH₃)—(CH₂CH₂OH)₂, —C(O)O—(CH₂)₂—N⁺(CH₃)—(CH₂CH₂OH)₂, —C(O)O—(CH₂)₃—N⁺(CH₃)—(CH₂CH₂OH)₂, —C(O)O—(CH₂)₄—N⁺(CH₃)—(CH₂CH₂OH)₂, —NH—(CH₂)₂—N—(CH₃)—(CH₂CH₂OH)₂, —NH—(CH₂)₃—N⁺(CH₃)—(CH₂CH₂OH)₂, —NH—(CH₂)₄—N⁺(CH₃)—(CH₂CH₂OH)₂, —O—(CH₂)₂—N(CH₃)—(CH₂CH₂OH)₂, —O—(CH₂)₃—N⁺(CH₃)—(CH₂CH₂OH)₂, —O—(CH₂)₄—N⁺(CH₃)—(CH₂CH₂OH)₂, —CH₂NH—(CH₂)₂—N⁺(CH₃)—(CH₂CH₂OH)₂, —CH₂NH—(CH₂)₃—N⁺(CH₃)—(CH₂CH₂OH)₂, —CH₂NH—(CH₂)₄—N⁺(CH₃)—(CH₂CH₂OH)₂, —CH₂CH₂NH—(CH₂)₂—N⁺(CH₃)—(CH₂CH₂OH)₂, —CH₂CH₂NH—(CH₂)₃—N⁺(CH₃)—(CH₂CH₂OH)₂, —CH₂CH₂NH—(CH₂)₄—N⁺(CH₃)—(CH₂CH₂OH)₂, -(1,4-phenylene)CH₂NH—(CH₂)₂—N⁺(CH₃)—(CH₂CH₂OH)₂, -(1,4-phenylene)CH₂NH—(CH₂)₃—N⁺(CH₃)—(CH₂CH₂OH)₂, -(1,4-phenylene)CH₂NH—(CH₂)₄—N⁺(CH₃)—(CH₂CH₂OH)₂, -(1,4-phenylene)NH—(CH₂)₂—N⁺(CH₃)—(CH₂CH₂OH)₂, -(1,4-phenylene)NH—(CH₂)₃—N⁺(CH₃)—(CH₂CH₂OH)₂, -(1,4-phenylene)NH—(CH₂)₄—N⁺(CH₃)—(CH₂CH₂OH)₂, -(1,4-phenylene)O—(CH₂)₂—N⁺(CH₃)—(CH₂CH₂OH)₂, -(1,4-phenylene)O—(CH₂)₃—N⁺(CH₃)—(CH₂CH₂OH)₂, or -(1,4-phenylene)O—(CH₂)₄—N⁺(CH₃)—(CH₂CH₂OH)₂ and any one of the boronic acids shown in FIG. 5. Preferred boronic acids are those prepared in Examples 1–10 and variants thereof in which the alkylene group has from 5 to 15 carbon atoms. In other specific examples of boronate functionalized monomers represented by Structural Formula (XV), -MQW comprises a boronate ester formed from —C(O)NH—(CH₂)₁CHOHCH₂OH, —C(O)NH—(CH₂)₂CHOHCH₂OH, —C(O)NH—(CH₂)₃CHOHCH₂OH, —C(O)O—(CH₂)₁CHOHCH₂OH, —C(O)O—(CH₂)₂CHOHCH₂OH, —C(O)O—(CH₂)₃CHOHCH₂OH, —NH—(CH₂)₁CHOHCH₂OH, —NH—(CH₂)₂CHOHCH₂OH, —NH—(CH₂)₃CHOHCH₂OH, —O(CH₂)₁CHOHCH₂OH, —O—(CH₂)₂CHOHCH₂OH, —O—(CH₂)₃CHOHCH₂OH, —CH₂NH—(CH₂)₁CHOHCH₂OH, —CH₂NH—(CH₂)₂CHOHCH₂OH, —CH₂NH—(CH₂)₃HOHCH₂OH, —CH₂CH₂NH—(CH₂)₁CHOHCH₂OH, —CH₂CH₂NH—(CH₂)₂CHOHCH₂OH, —CH₂CH₂NH—(CH₂)₃CHOHCH₂OH, -(1,4-phenylene)CH₂NH—(CH₂)₁CHOHCH₂OH, -(1,4-phenylene)CH₂NH—(CH₂)₂CHOHCH₂OH, -(1,4-phenylene)CH₂NH—(CH₂)₃CHOHCH₂OH, -(1,4-phenylene)NH—(CH₂)₁CHOHCH₂OH, -(1,4-phenylene)NH—(CH₂)₂CHOHCH₂OH, -(1,4-phenylene)NH—(CH₂)₃CHOHCH₂OH, -(1,4-phenylene)O—(CH₂)₁CHOHCH₂OH, -(1,4-phenylene)O—(CH₂)₂CHOHCH₂OH or -(1,4-phenylene)O—(CH₂)₃CHOHCH₂OH, and any one of the boronic acids shown in FIG. 5. Preferred boronic acids are those prepared in Examples 1–10 and variants thereof in which the alkylene group has from 5 to 15 carbon atoms.

The polymers of the present invention can be homopolymers, which have a uniform backbone composed of a boronate functionalized monomers derived from a common polymerizable unit, such as boronate functionalized acrylamide. Also included are copolymers and terpolymers, i.e., polymers comprising a mixed backbone of two or three different monomer units, respectively, one or more of which is boronate functionalized.

"Polymer backbone" or "backbone" refers to that portion of the polymer which is a continuous chain, comprising the bonds which are formed between monomers upon polymerization. The composition of the polymer backbone can be described in terms of the identity of the monomers from which it is formed, without regard to the composition of branches, or side chains, off of the polymer backbone. Thus, a poly(acrylamide) polymer is said to have a poly(acrylamide) backbone, without regard to the substituents on the acrylamide nitrogen atom, which are components of the polymer side chains. A poly(acrylamide-co-styrene) copolymer, for example, is said to have a mixed acrylamide/styrene backbone.

A "side-chain" refers to a branch off of the polymer backbone.

Preferred polymers are "fat binding" polymers. "Fat-binding polymers" are polymers which absorb, bind or otherwise associate with fat thereby inhibiting partially or completely) fat digestion, hydrolysis, or absorption in the gastrointestinal tract and/or facilitate the removal of fat from the body prior to digestion. The fat-binding polymers comprise one or more fat-binding regions. "Fat-binding regions" include a positively charged region, and, optionally, a hydrophobic region, or a region which is both positively charged and hydrophobic. The fat-binding region has a positive charge when the region comprises an ionic group such as a quarternary amine or an atom, for example, the nitrogen of an amine, that possesses a positive charge under conditions present in the gastrointestinal tract. Guidance on preparing and selecting suitable fat-binding polymers can be found in, for example, U.S. Pat. Nos. 5,487,888, 5,496,545, 5,607,669, 5,618,530, 5,624,963, 5,667,775, and 5,679,717 and co-pending U.S. applications having Ser. Nos 08/353,329, 08/166,453, 08/471,747, 08/482,969, 08/567,933, 08/659,264, 08/823,699, 08/835,857, 08/470,940, 08/461,298, 08/826,197, 08/777,408, 08/927,247, 08/964,956, 08/964,498, and 08/964,536, the entire contents of all of which are incorporated herein by reference.

The polymers of the present invention include addition polymers such as a boronate functionalized polyacrylate, alkylpolyacrylate, polyacrylamide, alkylpolyacrylamide, poly(allylalcohol), poly(vinylalcohol), poly(vinylamine), poly(allylamine), poly(diallylamine) backbone or a substituted polystyrene backbone. Typically, these addition polymers have side chains comprising aryl boronate groups formed from an alkyldiol, a diethanolamine, or aminoalkyldiol and an aryl boronic acid. The side chains are attached, for example, by ester linkages to carboxylate groups of a polyacrylate, by a covalent bond to the amide nitrogens of a polyacrylamide, by ether linkages to alcohols of a poly (vinylalcohol) or poly(allylalcohol), by a covalent bond to the amines of a poly(vinylamine,) a poly(allylamine) or a poly(diallylamine) or by a covalent bond to a substituent on the phenyl ring of a polystyrene. Polyacrylamide is a preferred polymer. Suitable addition polymers are described below.

In one aspect, the polymer comprises monomers having both cationic and hydrophobic groups. For example, fat-binding polymers of this type can be a homopolymer, copolymer or terpolymer comprising a boronate functionalized monomer with an diethanolamine or aminoalkyldiol in the polymer side chains, as in Structural Formulas (VIII), (X) and (XII) (or the corresponding ammonium groups in Structural Formulas (IX), (XI) and (XIV)), provided that the side chain comprises a hydrophobic group (e.g., wherein M in Structural Formula (XV) is a hydrophobic group). The term "hydrophobic group" is defined below. The diethanolamine or aminoalkyldiol comprises an amine which can be protonated in vivo to form a cationic group. Another example of a fat-binding polymer of this type is a copolymer or terpolymer comprising a boronate functionalized monomer and a monomer having both cationic and hydrophobic groups. Aliphatic amine monomers in which the amine has at least one hydrophobic alkyl substituent, such as an alkyl group with between about four and thirty carbons, has both a hydrophobic region and a positively charged region in combination. Additional aliphatic amine monomers are described below.

In another aspect, the fat-binding polymer comprises boronate functionalized monomers together with a combination of separate monomers each having either a cationic or a hydrophobic functional groups. Examples of monomers having a cationic group and monomers having hydrophobic groups are provided below.

In another aspect, the fat-binding polymer comprises monomers having both cationic and neutral functional groups (e.g., a hydroxy group or a carboxamide group). Fat-binding polymer of this type include homopolymers, copolymers or terpolymers comprising a boronate functionalized monomer with a diethanolamine or an aminoalkyldiol in the polymer side chains, as in Structural Formulas (VIII), (XI) and (XIII) (or the corresponding ammonium groups in Structural Formulas (IX), (XI) or (XIV). The aminoalkyldiol comprises an amine which can be protonated in vivo and diols which are released when the boronate ester is hydrolyzed. Alternatively, the fat-binding polymer of this type is a co-polymer or terpolymer comprising a boronate functionalized monomer and a monomer have both a neutral and a cationic functional group. Examples of monomers of this type include aliphatic amine monomers wherein the amine group is derivatized with a hydroxy alkyl group (e.g., N-(ω-hydroxyalkyl)allylamine and N-(ω-hydroxyalkyl)vinylamine).

Alternatively, the fat-binding polymer comprises a combination of separate monomers each having either a cationic or a neutral functional group. As noted above, hydrolysis in the gastrointestinal tract of the phenyl boronate ester of a boronate functionalized monomer "releases" a diol functionality. Thus, fat-binding polymers of this type include copolymers comprising a boronate functionalized monomer and a cationic monomer such an aliphatic amine monomer. In another example, the fat-binding polymer is a terpolymer comprising a boronate functionalized monomer, a cationic monomer (e.g., an aliphatic amine monomer) and a neutral co-monomer (e.g., vinyl alcohol, allyl alcohol and acrylamide).

Cationic monomers include monomers which contain amine groups, i.e., "amine monomers". Specific examples of aliphatic amine monomers found in addition polymers include allylamine, diallylamine, diallylmethylamine and vinylamine. Other amine monomers include aminostyrene, vinylimidazolyl, vinylpyridinyl, dimethylaminomethylstyrene and diallylmethylammonium chloride. Yet other examples of amine monomers include amine or quaternary amine-containing moieties used in conjunction with acrylate or acrylamide polymers. Examples include aminoalkyl esters or ammoniumalkyl (e.g., trialkylammonium alkyl) esters of an acrylate monomer (e.g., trimethylammonium ethyl methacrylate and trimethylammonium ethyl acrylate) or N-aminoalkyl amide or N-ammoniumalkyl amides (e.g., N-trialkylammonium alkyl) of acrylamides (e.g., N-trimethylammonium ethyl methacryamide and N-trimethylammonium ethyl acrylamide).

As noted above, an amine monomer can comprise one or more hydrophobic regions which are bound to the amine nitrogen of the amine monomer to form a monomer with both a cationic and hydrophobic group. Examples include N-(C4–C30)alkylvinylamine, N-(C4–C30)alkylallylamine, N-(C4–C30)alkyldiallylamine, N-(C4–C30)alkylaminostyrene and N,N-(C1–C30)dialkylaminostyrene.

Hydrophobic monomers are monomers which lack a cationic group and comprise a hydrophobic group. Examples include styrene, (C6–C30) olefinic monomers (e.g., hexene, heptene, octene), (C4–C30)alkylacrylates, (C4–C30)alkylmethacrylates, N-(C4–C30)alkylacrylamides, N-(C4–C30)alkylmethacrylamides, styrene (e.g., fluorstyrene and pentaflourostyrene), vinylnaphthalene, ethylvinylbenzene, vinylbiphenyl, vinylanisole.

Optionally, fat-binding polymers can comprise hydrophilic monomers. Examples include acrylic acid, methacrylic acid, acrylamide and methacrylamide.

The present invention also includes condensation polymers, which are formed from reactions in which a small molecule such as water is released. Examples include a polyamide, polyalkyleneimine or a polyester. The cationic groups in a polyalkyleneimine can be the amine or ammonium nitrogens in the backbone or, alternatively ammoniumalkyl (e.g., a trialkylammonium alkyl group) or hydroxylated alkyl (e.g., hydroxyethyl) bonded to nitrogen in the polymer backbone or an amine group in the side chain connecting the boronate ester to a nitrogen in the backbone. The hydrophobic group can be a C4–C30 alkylene group in the polymer backbone, a hydrophobic alkyl group bonded to a backbone nitrogen atom or a hydrophobic spacer group Q, between nitrogen in the backbone and W, wherein Q and W are as defined above. For polyamides, a group -Q-W can be bonded to amide nitrogens in the polymer backbone, wherein Q and W are as defined above and are selected such that Q is hydrophobic and W comprises a diethanolamine or an aminoalkyldiol or the corresponding ammonium compounds, as shown in Structural Formulas (V)–(XIV). For polyesters, a group -Q-W can be bonded to a carbon atom in the backbone wherein Q and W are as defined above and are selected such that Q is hydrophobic and W comprises a diethanolamine or an aminoalkyldiol or the corresponding ammonium compounds, as shown in Structural Formulas (V)–(XIV).

The polymer can be linear or crosslinked. Crosslinking can be performed by reacting the copolymer with one or more crosslinking agents having two or more functional groups, such as electrophilic groups, which react with, for example, amine groups to form a covalent bond. Crosslinking in this case can occur, for example, via nucleophilic attack of the polymer amino groups on the electrophilic groups. This results in the formation of a bridging unit which links two or more amino nitrogen atoms from different polymer strands. Suitable crosslinking agents of this type include compounds having two or more groups selected from among acyl chloride, epoxide, and alkyl-X, wherein X is a suitable leaving group, such as a halo, tosyl or mesyl group. Examples of such compounds include, but are not limited to, epichlorohydrin, succinyl dichloride, acryloyl chloride, butanedioldiglycidyl ether, ethanedioldiglycidyl ether, pyromellitic dianhydride, and dihaloalkanes. These crosslinking agents are referred to herein as multifunctional crosslinking agents.

The polymer composition can also be crosslinked by including a multifunctional co-monomer as the crosslinking agent in the polymerization reaction mixture. A multifunctional co-monomer can be incorporated into two or more growing polymer chains, thereby crosslinking the chains. Suitable multifunctional co-monomers include, but are not limited to, diacrylates, triacrylates, and tetraacrylates, dimethacrylates, diacrylamides, and dimethacrylamides. Specific examples include ethylene glycol diacrylate, propylene glycol diacrylate, butylene glycol diacrylate, ethylene glycol dimethacrylate, butylene glycol dimethacrylate, methylene bis(methacrylamide), ethylene bis(acrylamide), ethylene bis(methacrylamide), ethylidene bis(acrylamide), ethylidene bis(methacrylamide), pentaerythritol tetraacrylate, trimethylolpropane triacrylate, bisphenol A dimethacrylate, and bisphenol A diacrylate. Other suitable multifunctional monomers include polyvinylarenes, such as divinylbenzene.

The amount of cross-linking agent is typically between about 0.01 and about 10 weight % based on the combined weight of crosslinking agent and monomers, with 0.1–3% being preferred. Typically, the amount of cross-linking agent that is reacted with the polymer, when the crosslinking agent is a multifunctional agent, is sufficient to cause between about 0.1 and 6 percent of the nucleophiles present on the monomer, for example, an amine to react with the crosslinking agent.

In addition, the polymers can be further characterized by one or more substituents such as substituted and unsubstituted, saturated or unsaturated alkyl, and substituted or unsubstituted aryl groups. Suitable groups to employ include cationic or neutral groups, such as alkoxy, aryl, aryloxy, aralkyl, halogen, amine, ammonium groups, substituted or unsubstituted oxypolyethylene oxide, and mono, di or higher hydroxyalkyl groups.

A "hydrophobic moiety (group)", as the term is used herein, is a moiety which, as a separate entity, is more soluble in octanol than water. For example, the octyl group ($C_8H_{17}$) is hydrophobic because its parent alkane, octane, has greater solubility in octanol than in water. The hydrophobic moieties can be a saturated or unsaturated, substituted or unsubstituted hydrocarbon group. Such groups include substituted and unsubstituted, normal, branched or cyclic alkyl groups having at least four carbon atoms, substituted or unsubstituted arylalkyl or heteroarylalkyl groups and substituted or unsubstituted aryl or heteroaryl groups. Preferably, the hydrophobic moiety includes an alkyl group of between about four and thirty carbons. Specific examples of suitable hydrophobic moieties include the following alkyl groups n-hexyl, n-heptyl, n-octyl, n-nonyl, n-decyl, n-undecyl, n-dodecyl, n-tetradecyl, n-octadecyl, 2-ethylhexyl, 3-propyl-6-methyl decyl, phenyl and combinations thereof. Other examples of suitable hydrophobic moieties include haloalkyl groups of at least six carbons (e.g., 10-halodecyl), hydroxyalkyl groups of at least six carbons (e.g., 11-hydroxyundecyl), and aralkyl groups (e.g., benzyl).

A "hydrophobic alkyl group", as that term is employed herein, includes a substituted or unsubstituted alkyl group having from four to about thirty carbons and which is hydrophobic, as earlier defined. The hydrophobic alkyl group can be, for example, normal or branched.

As used herein, aliphatic groups include straight chained, branched or cyclic C1–C30 (preferably C5–C22) hydrocarbons which are completely saturated or which contain one or more units of unsaturation. Preferred aliphatic groups are completely saturated and acyclic, i.e., straight chained or branched alkyl groups. Suitable substituents for an aliphatic group are those which do not significantly lower the lipase inhibiting ability or fat binding ability of the polymer, for example, do not lower either activity by more than a factor of about two. Examples include —OH, halogen (—Br, —Cl, —I and —F), —O(R'), —O—CO—(R'), —CN, —NO₂, —COOH, =O, —NH₂, —NH(R'), —N(R')₂, —COO(R'), —CONH₂, —CONH(R'), —CON(R')₂, —SH and —S(R'). Each R' is independently an alkyl group or an aryl group. A substituted aliphatic group can have more than one substituent.

Aryl groups include carbocyclic aromatic groups such as phenyl and naphthyl, heteroaryl groups such as imidazolyl, thienyl, furanyl, pyridyl, pyrimidy, pyranyl, pyrazolyl, pyrazinyl, thiazole, oxazolyl and fused polycyclic aromatic ring systems in which a carbocyclic aromatic ring or heteroaryl ring is fused to one or more other heteroaryl rings (e.g., benzothienyl, benzofuranyl, indolyl, quinolinyl, benzothiazole, benzooxazole, benzimidazole and quinolinyl). Suitable substituents for an aryl group are those which do not significantly lower the lipase inhibiting ability or fat binding ability of the polymer, for example, do not lower either activity by more than a factor of about two. Examples include alkyl, halogenated alkyl, —OH, halogen (—Br, —Cl, —I and —F), —O(R'), —O—CO—(R'), —CN, —NO₂, —COOH,—NH₂, —NH(R'), —N(R')₂, —COO(R'), —CONH₂, —CONH(R'), —CON(R')₂, —SH and —S(R'). Each R' is independently an alkyl group or an aryl group. A substituted aryl group can have more than one substituent.

Non-aromatic nitrogen-containing, heterocyclic rings are non-aromatic carbocyclic rings which include at least one nitrogen atom and, optionally, one or more other heteroatoms such as oxygen or sulfur in the ring. The ring can be five, six, seven or eight-membered. Examples include morpholino, thiomorpholino, pyrrolidinyl, piperazinyl and piperidinyl.

In the structural formulas depicted herein, the single or double bond by which a chemical group or moiety is connected to the remainder of the molecule or compound is indicated by the following symbol:

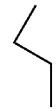

For example, the corresponding symbol in Structural Formulas (I) and (II) boronate ester bond by which the phenylboronate group is connected to the polymer.

Also included in the present invention are pharmaceutically acceptable salts of the disclosed polymers. For example, polymers which have acid functional groups can also be present in the anionic, or conjugate base, form, in combination with a cation. Suitable cations include alkaline earth metal ions, such as sodium and potassium ions, alkaline earth ions, such as calcium and magnesium ions, and unsubstituted and substituted (primary, secondary, tertiary and quaternary) ammonium ions. Polymers which have basic groups such as amines can also be protonated with a pharmaceutically acceptable counter anion, such as chloride, bromide, acetate, formate, citrate, ascorbate, sulfate or phosphate. Similarly, ammonium groups similarly comprise a pharmaceutically acceptable counteranion. Boronic acid groups can react with anions such as sodium or potassium hydroxide, alkoxide or carboxylate to form a salt such as —B⁻(OH)₃Na⁺, —B⁻(OH)₃K⁺, —B⁻(OH)₂(OCH₃)Na⁺, —B⁻(OH)₂(OCH₃)K⁺, —B⁻(OH)₂(OCOCH₃)Na⁺, —B⁻(OH)₂(OCOCH₃)K⁺, and the like The positive charge of ammonium groups in the disclosed polymers are counterbalanced with a suitable counteranion such as $Cl^-$, $Br^-$, $I^-$, $NO_3^-$, $HSO_4^-$, $CO_3^{-2}$, $HCO_3^-$ or $SO_4^{-2}$. The counteranions on a polymer can be the same or different. An anion with a charge greater than one will counterbalance the positive charge of more than one ammonium group.

A "subject" is preferably a mammal, such as a human, but can also be a companion animal (e.g., dogs, cats, and the like), farm animals (e.g., cows, sheep, pigs, horses, and the like) or laboratory animals (e.g., rats, mice, guinea pigs, and the like) in need of treatment for obesity.

The polymers of the present invention are suitable as a medicament for promoting weight reduction in mammals because they inhibit lipases and bind fat molecules such as diglycerides and triglycerides, in the gastrointestinal tract. As such, they are administered in a manner suitable for reaching the gastrointestinal tract during digestion. They are therefore preferably administered orally as soon as up to about one hour prior to a meal and as late as to up to about one hour subsequent to a meal. Preferably, the polymer of sufficiently high molecular weight to resist absorption, partially or completely, from the gastrointestinal tract into other parts of the body. The polymers can have molecular weights ranging from about 500 Daltons to about 500,000 Daltons, preferably from about 2,000 Daltons to about 150,000 Daltons. In the polymers represented herein by structural formulas, e.g., Structural Formula (XV), "n" represents an integer chosen such that the polymer has the desired molecular weight.

The polymers of the present invention are administered to inhibit of uptake of fat in the gastrointestinal tract (or to promote removal of fat from the gastrointestinal tract). Thus, they can be also be advantageously used to in the treatment or one or more of the following conditions: obesity, Type II (non-insulin-dependent) diabetes mellitus, impaired glucose tolerance, hypertension, coronary thrombosis, stroke, lipid syndromes, hyperglycemia, hypertriglyceridemia, hyperlipidemia, sleep apnea, hiatal hernia, reflux esophagisitis, osteoarthritis, gout, cancers associated with weight gain, gallstones, kidney stones, pulmonary hypertension, infertility, cardiovascular disease, above normal weight, and above normal lipid levels; or where the subject would benefit from reduced platelet adhesiveness, weight loss after pregnancy, lowered lipid levels, lowered uric acid levels, or lowered oxalate levels. A subject with one or more of these conditions is said to be "in need of treatment" with an agent that inhibits absorption of fat from the gastrointestinal tract.

An "effective amount" is the quantity of polymer which results in a greater amount of excretion of fat from the gastrointestinal tract over a period of time during which a subject is being treated with the polymer drug compared with the corresponding time period in absence of such treatment. When the subject is being treated for obesity, an "effective amount" is the quantity of polymer which results in a greater amount of weight reduction over a period of time during which a subject is being treated with the polymer drug compared with the corresponding time period in absence of such treatment. Typical dosages range from about 5 milligrams/day to about 10 grams/day, preferably from about 50 milligrams/day to about 5 grams/day. The polymer can be administered alone or in a pharmaceutical composition comprising the polymer, an acceptable carrier or diluent and, optionally, one or more additional drugs, typically one or more additional drugs used for weight reduction (e.g., XENICAL or MERIDIA). Typically, the pharmaceutical composition comprises an effective concentration of the polymer, which is a concentration which can administer an effective amount of the polymer.

The precise amount of polymer being administered to a subject will be determined on an individual basis and will depend on, at least in part, the subject's individual characteristics, such as general health, age, sex, body weight and tolerance to drugs, and the degree to which the subject is overweight and the amount of weight reduction sought.

The disclosed polymers can be administered to the subjects in conjunction with an acceptable pharmaceutical carrier as part of a pharmaceutical composition for treatment of obesity. Formulations vary according to the route of administration selected, but for oral administration are typically capsule. Solutions and emulsions are also possible. Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. s for encapsulating compositions (such as in a coating of hard gelatin or cyclodextran) are known in the art (Baker, et al., "Controlled Release of Biological Active Agents", John Wiley and Sons, 1986).

Figure 4:
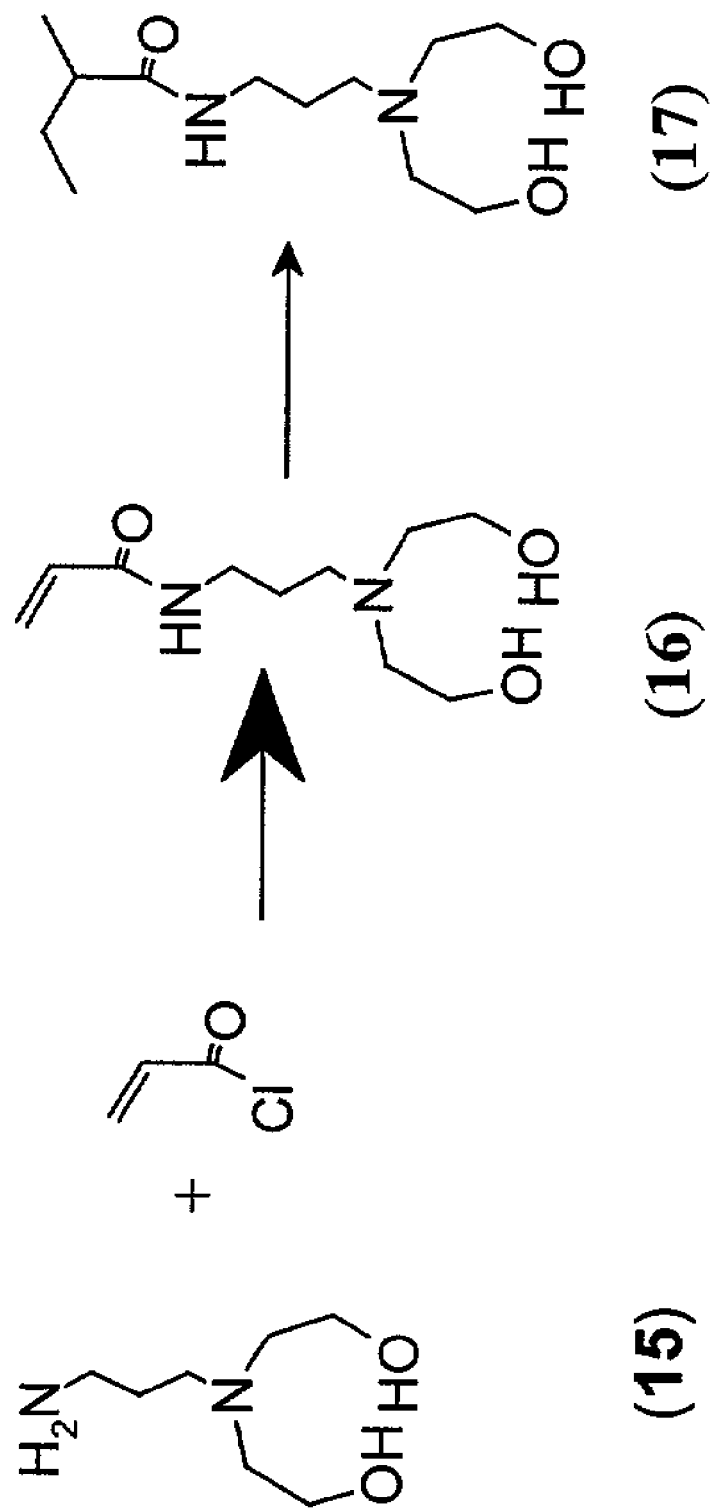
FIG. 4 is a schematic showing the synthesis of poly-N-(3-diethanolaminopropyl)acrylamide (17).
Figure 5A:
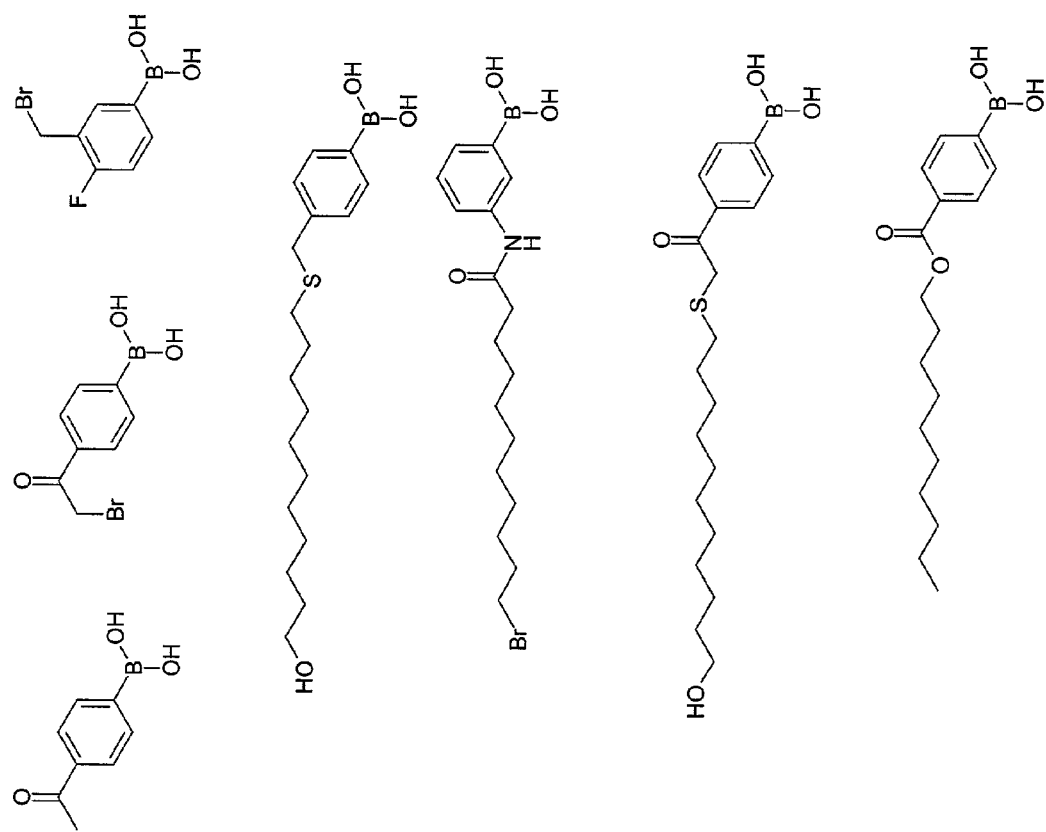
FIGS. 5A–5F are a compilation of the structures of boronic acids which can be incorporated into the boronate functionalized polymers of the present invention. R in FIG. 5D is a C12 straight chained alkyl group.
Figure 5B:
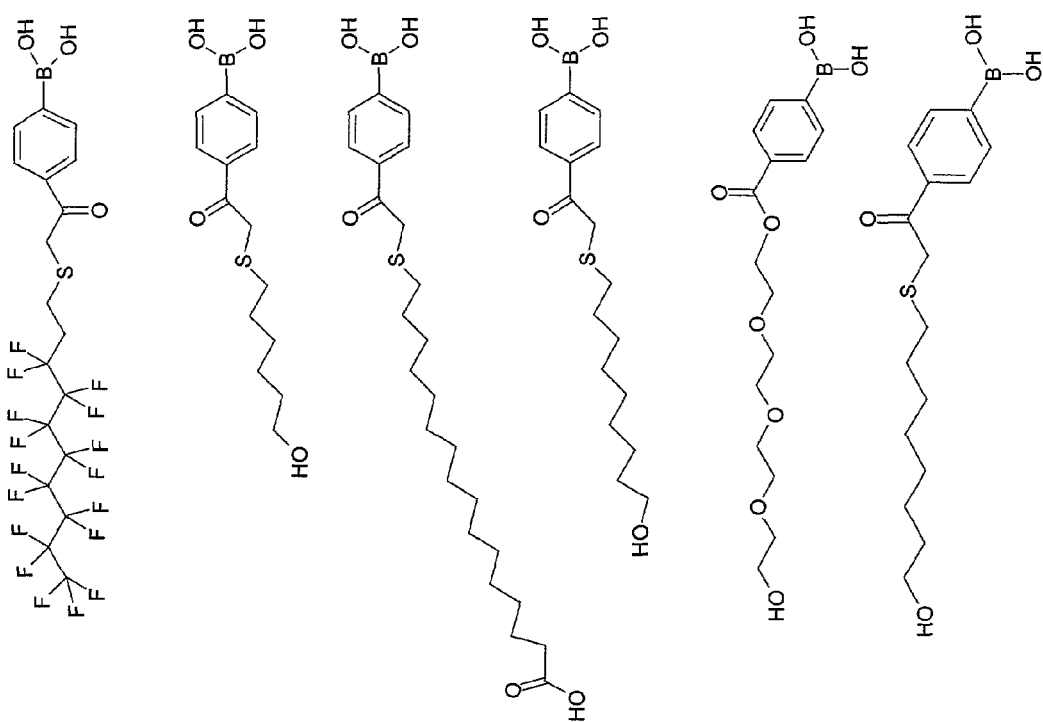
Figure 5C:
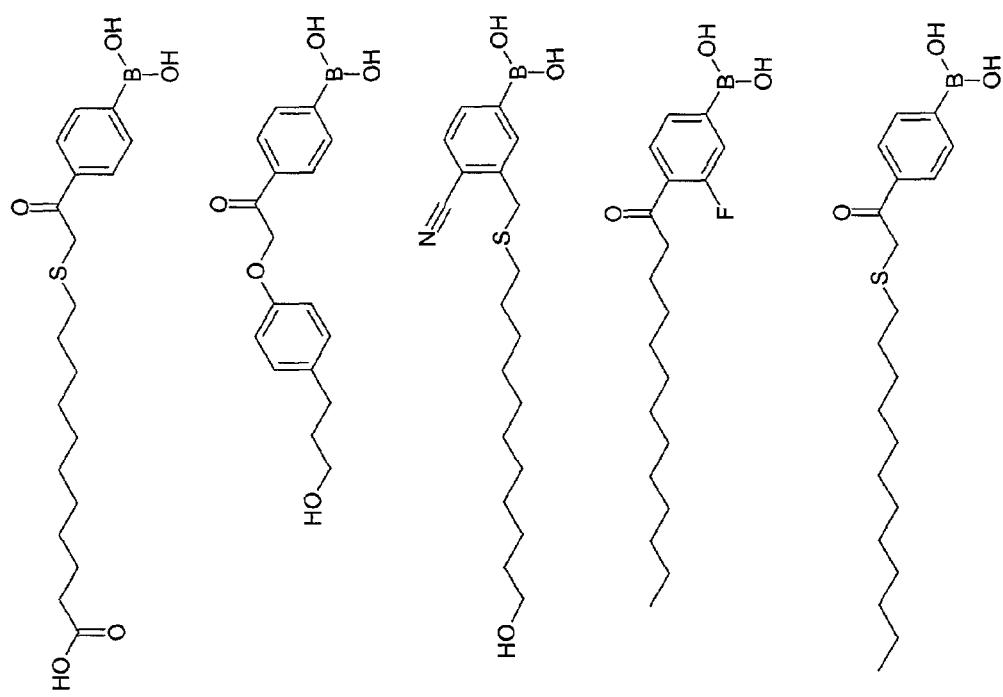
Figure 5D:
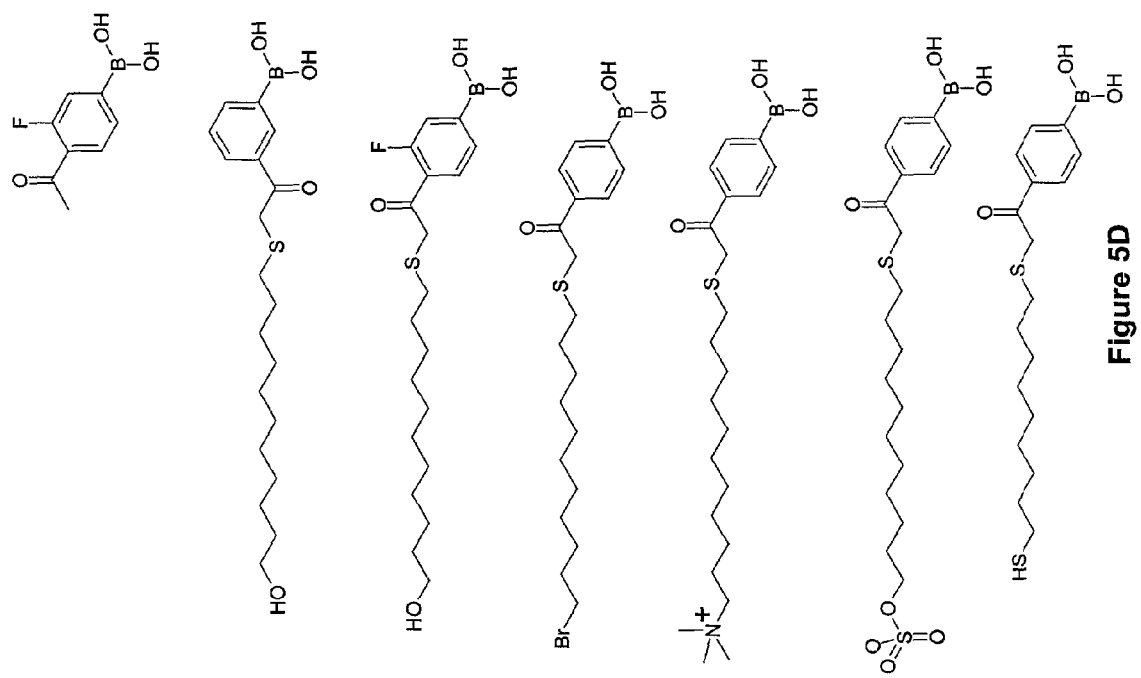
Figure 5E:
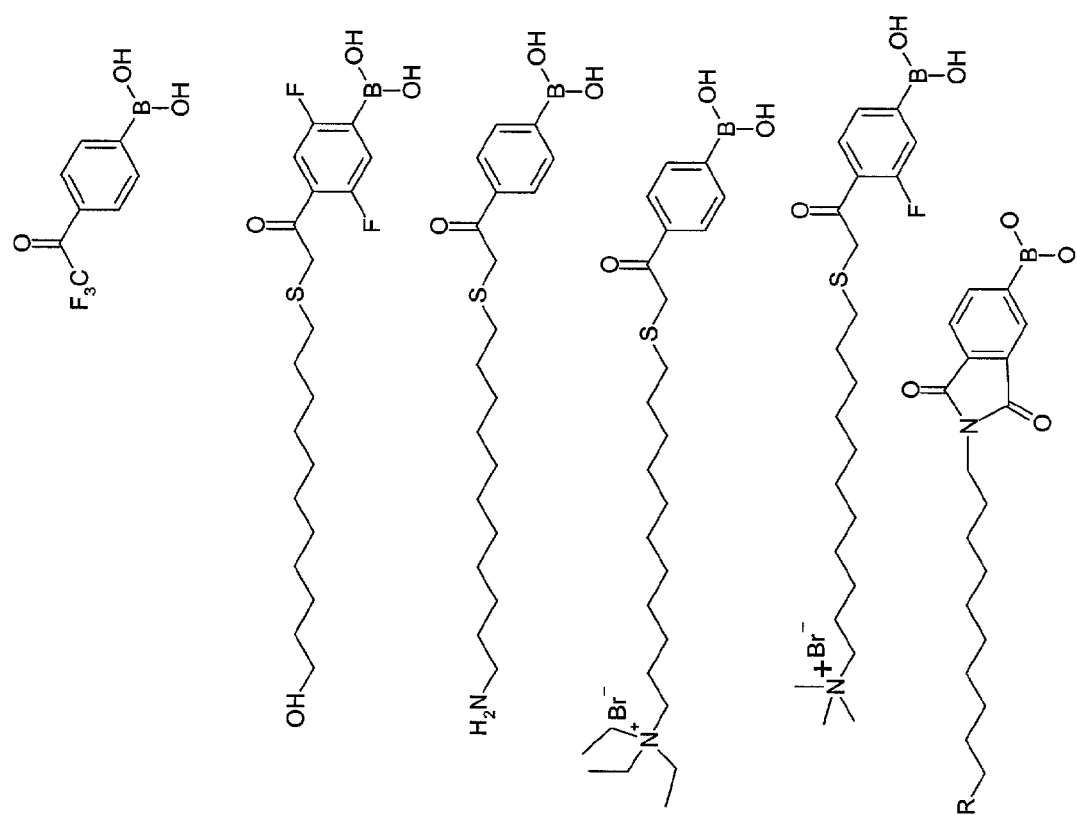
Figure 5F:
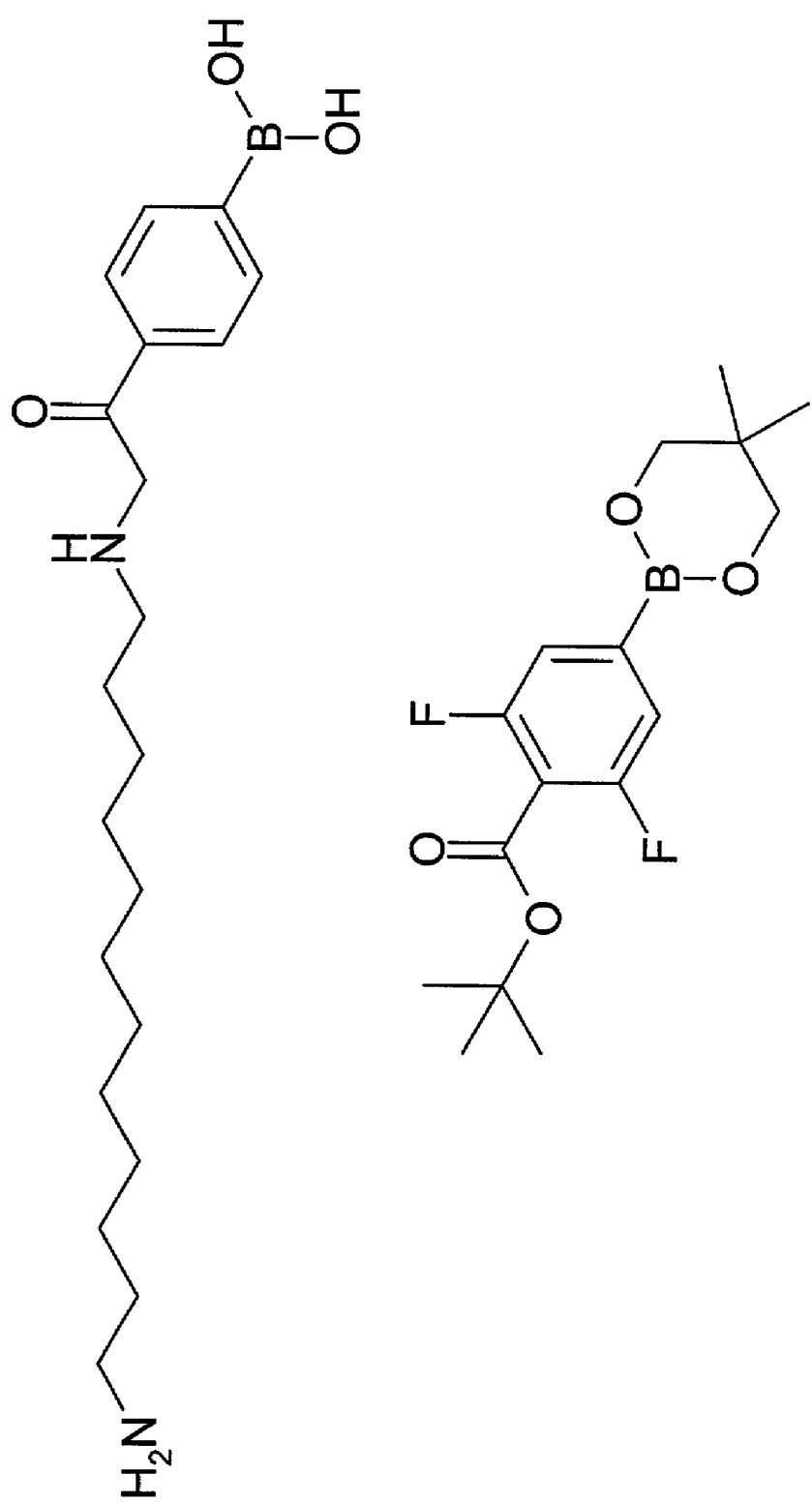

The polymer of the present invention can be prepared by synthesizing monomer comprising side chains with diethanol amine alkyldiol or aminoalkyldiol groups, as is described, for example, in Example 11 and shown schematically in FIG. 4, and then polymerizing. A suitable aryl boronic acid is prepared and then coupled to the diol groups in the polymer product. Alternatively, boron functionalized monomers are prepared and then polymerized according to standard means.

The polymerization includes direct polymerization of a diethanol amine alkyldiol or aminoalkyldiol functionalized monomer (or boron functionalized) or with a set of monomers, one of which is diethanolamine, alkyldiol or aminoalkyldiol functionalized (or boron functionalized). This can be accomplished via standard s of free radical, cationic or anionic polymerization which are well known in the art. Due to reactivity differences between two monomers, the composition of a copolymer produced in this way can differ from the composition of the starting mixture. This reactivity difference can also result in a non-random distribution of monomers along the polymer chain.

Figure 2:
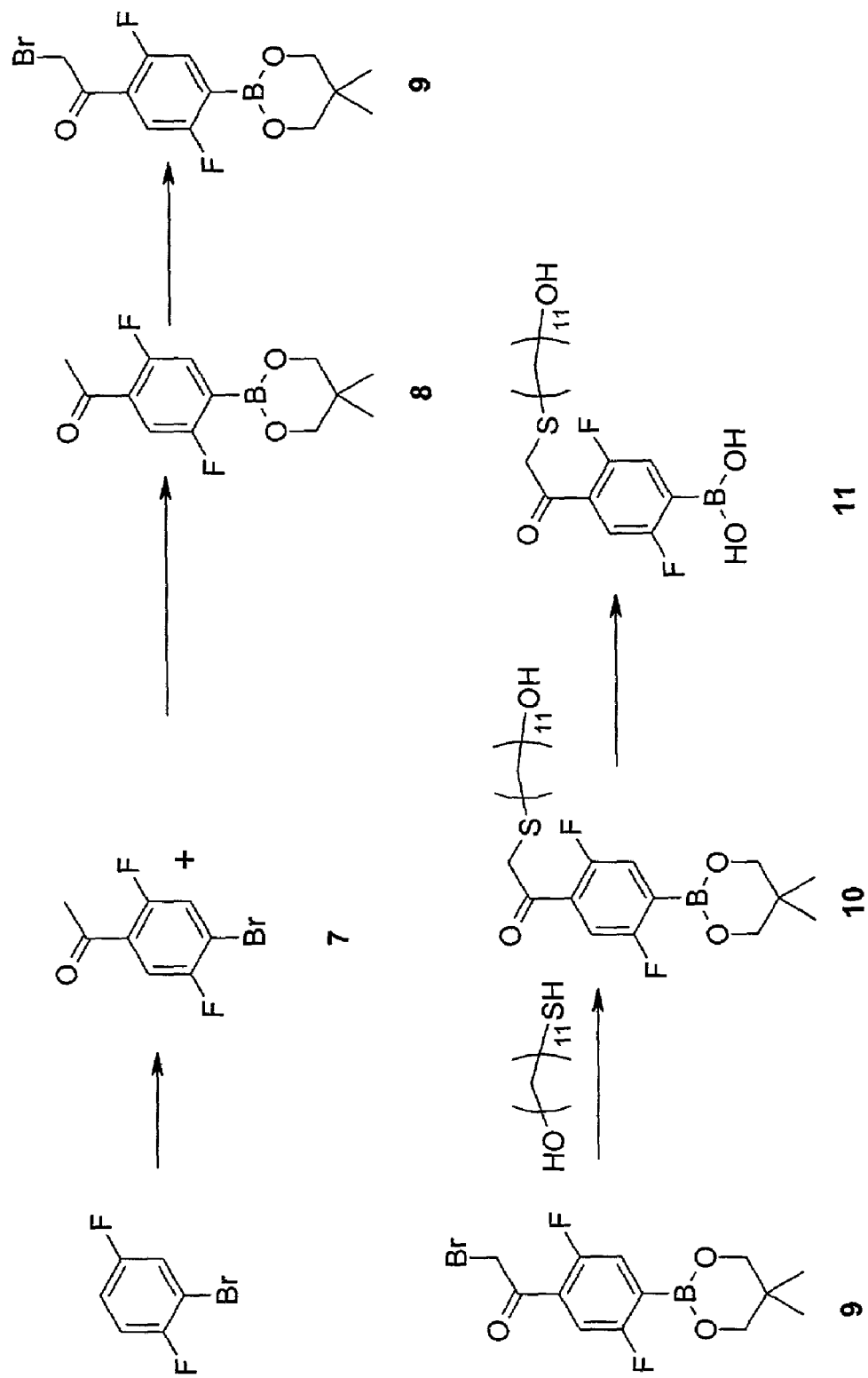
FIG. 2 is a schematic showing the synthesis of 4-(14'-hydroxy-3'-thia-1'-ketotetradecyl)-2,5-difluorophenylboronic acid (11).
Figure 3:
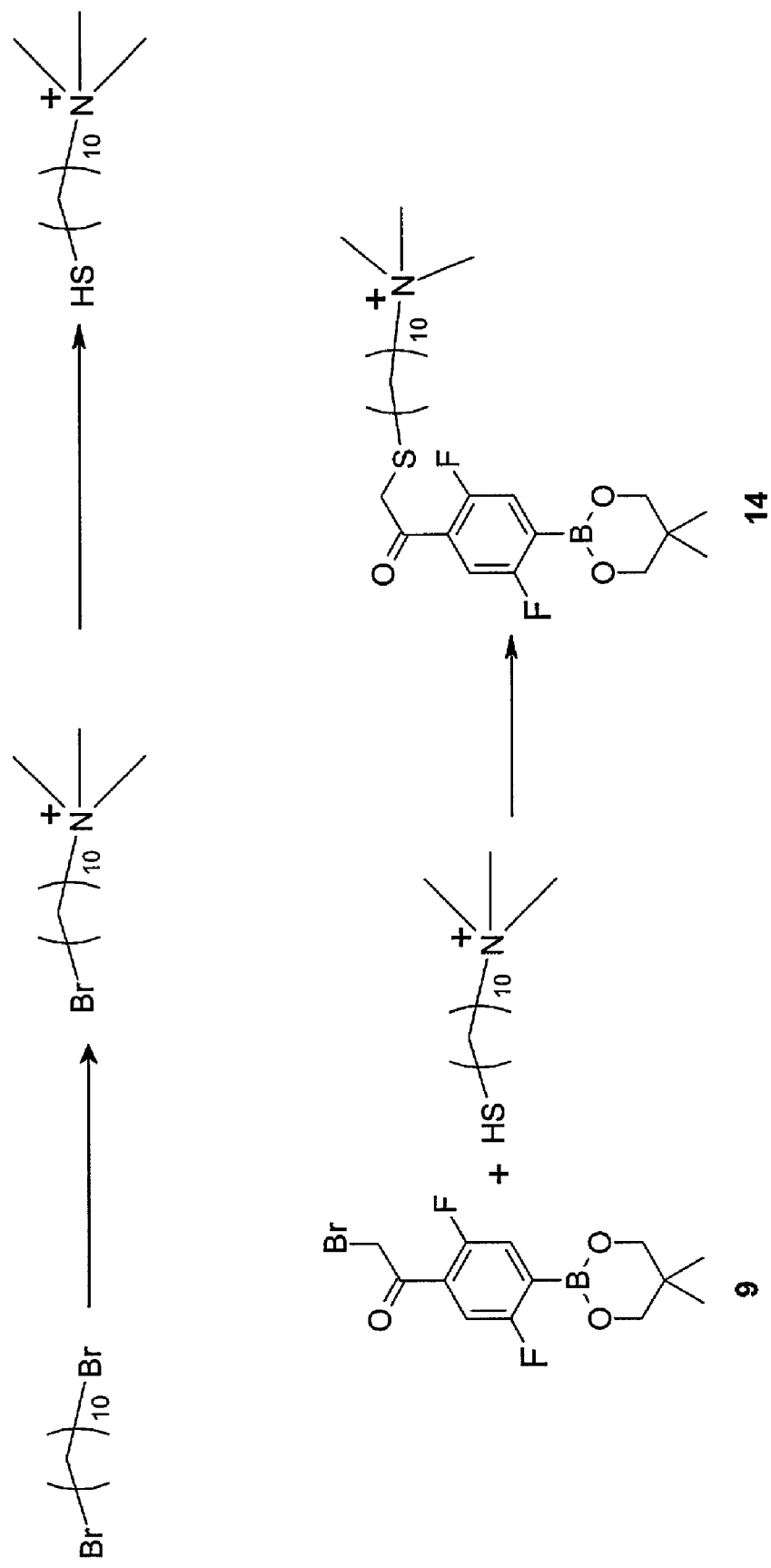
FIG. 3 is a schematic showing the synthesis of (neopentyl glycolato) 4-(14'-trimethylammonium-3'-thia-1'-ketotridecyl)-2,5-difluorophenylboronate ester chloride (14).

The preparation of representative phenyl boronic acid compounds is described in Examples 1–10 and shown schematically in FIGS. 1–3. The person of ordinary skill in the art will be able to select suitable starting materials to obtain the desired aryl boronic acid and, when carrying out these reactions with different starting materials to modify reaction conditions, if necessary, using no more than routine experimentation. For example, the 4-bromoacetophenone in FIG. 2 (Compound 7) can be replaced with any suitable aryl compound substituted with bromine or iodine and acetyl. For example, 2-Acetyl-5-bromothiophene is commercially available from the Aldrich Chemical Co., Milwaukee, Wis. The length of the hydrocarbyl group in the aryl boronic acids can be varied according to the length of the 1,ω-alkanethioalcohol.

Representative boronic acids of the present invention that have been prepared according to s described in the examples are shown in FIG. 5.

The preparation of diethanolamino functionalized polymers is described in Example 11 and shown schematically in FIG. 4.

The esterification of diol groups with aryl boronic acids can be carried out be s known in the art, for example, by reacting in suitable solvent, e.g., alcohol, toluene, methylene chloride, tetrahydrofuran or dimethylsulfoxide. Specific conditions are provided in Example 12. Analogous conditions can be used to esterify diol groups in monomers comprising diethanolamine, alkyldiol or aminoalkyldiol side chains. Alternatively, a transesterification reaction can be used to prepare a boronate ester from a boronic acid and polymer comprising a diethanolamine, alkyldiol or aminoalkyldiol side chains, for example, as is disclosed in D. H. Kinder and M. M. Ames, *Journal of Organic Chemistry* 52:2452 (1987) and D. S. Matteson and R. Ray, *Journal of American Chemical Society* 102:7590 (1980). The entire teachings of these references are incorporated herein by reference.

The invention is further illustrated by the following examples which are not intended to be limiting in any way.

EXEMPLIFICATION

Example 1

4-(14'-trimethylammonium-3'-thia-1'-ketotetradecyl)-3-fluorophenylboronic acid chloride (6)

The synthesis of Compound (6) is shown out schematically in FIG. 1. A detailed description of the procedure is provided below.

Step 1. Synthesis of 4-acetyl-3-fluorophenylboronic acid (1).

An oven-dried, 3-liter, 3-necked, round-bottomed flask (fitted with a nitrogen inlet, addition funnel, and overhead stirrer) was charged with 50 grams (0.25 mole) of 4-cyano-3-fluorophenyl bromide. Anhydrous tetrahydrofuran (200 milliliters) was added to the flask resulting in a clear solution. The solution was cooled to 0° C. using an ice bath. At this temperature, 125 milliliters of 3.0 M solution of $CH_3MgBr$ in ether (1.5 equivalents, 0.375 mole) was added slowly to the reaction flask using an addition funnel. The reaction mixture was allowed to slowly warm up to room temperature and was stirred for 48 hours. Thin layer chromatography (TLC) indicated the starting material was consumed. After 48 hours, the reaction was cooled down to −78° C. using an isopropanol/dry ice bath. At −78° C., 50 milliliters of 10.0 M solution of butyllithium in hexane (2.0 equivalents, 0.5 mole) was added to the reaction mixture with continuing stirring. An additional 400 milliliters of THF was added to ensure that reaction mixture was homogeneous and was stirring well. The reaction mixture was stirred at −78° C. for 3 hours. To the reaction mixture was added 170 milliliters of trimethylborate (6.0 equivalents, 1.5 mole) slowly using an addition funnel and the temperature was maintained at −78° C. While stirring, the reaction mixture was allowed to warm up to room temperature overnight. The progress of the reaction was monitored by TLC. After cooling the reaction mixture to 0° C. (using an ice bath) the contents were transferred into a 5 liter beaker. The flask was rinsed with 100 milliliters of methanol and the washing was combined with the reaction mixture. To the reaction mixture, 500 milliliters of 1 N HCl was slowly added. Subsequently, the pH of the mixture was brought to 4 by the addition of concentrated HCl. The reaction mixture was stirred for 3 hours. The organic solvent was removed by rotary evaporator. The concentrated aqueous content was extracted with ether (250 milliliter×6). The combined organic layer was washed with brine solution (200 milliliter×2) and was dried over $MgSO_4$. After filtration, ether was removed by rotary evaporator. The residue was recrystallized from hot water yielding an off white solid. Yield: 22 grams (50%).

Step 2. Synthesis of 4-(2'-bromoacetyl)-3-fluorophenylboronic acid (2).

An oven-dried, 500-milliliter, 3-necked, round-bottomed flask was charged with 5 grams (27.4 millimole) of 4-acetyl-3-fluorophenyl boronic acid and 25 milliliters of methanol under a nitrogen atmosphere. The solution was cooled to 0° C. using an ice bath. To this solution was added 0.2 milliliters (0.55 equivalents) of glacial acetic acid. In a 100 milliliters Erlenmeyer flask was taken 1.27 milliliters (3.95 grams, 24 millimole, 0.9 equivalents) of elemental bromine dissolved in 4 milliliters of cold methanol. The bromine solution was added dropwise to the above solution at 0° C. using an addition funnel. With the addition of $Br_2$, the solution slowly turned light orange and finally to dark orange when addition was complete. After about 5–6 hours, the progress of the reaction was monitored by NMR. Depending on the progress of reaction, another 10–20 mole % of bromine was added after cooling the solution to 0° C. Total reaction time was approximately 24 hours.

After completion of the reaction, the solvent was removed using rotary evaporator. The residue was dissolved in 200 milliliters of ethyl acetate. It was washed with deionized water (50 milliliters×3) and with brine (50 milliliters×2). The organic layer was collected and dried over anhydrous sodium sulfate for 1 hour. The solution was filtered and the solvent was removed using rotary evaporator. The residue was recrystallized from hot ethyl acetate. Yield=7 grams (97%).

Step 3. Synthesis of 4-(14'-hydroxy-3'-thia-1'-ketotetradecyl)-3-fluorophenylboronic acid (3).

An oven-dried, 500-milliliter, three-necked, round-bottomed flask was charged with 5 grams (19.15 millimole) of 4-(2'-bromoacetyl)-3-fluorophenylboronic acid (2) and 50 milliliters of anhydrous THF. The solution was flushed with $N_2$ for at least 30 minutes. To this solution was added 3.9 grams (19.15 millimole, 1 equivalent) of 11-mercaptoundecanol. While stirring under $N_2$, 6.62 milliliters (38.3 millimole, 2 equivalents) of diisopropylethylamine was added slowly. The reaction mixture was stirred at room temperature for 24 hours under nitrogen atmosphere. The progress of the reaction was monitored by TLC and NMR (after washing up the aliquot with 1 N HCl). If the reaction was not complete, additional (as required) 11-mercaptoundecanol was added and the reaction was allowed to proceed for another 24 hours. After completion of the reaction, the solvent was evaporated. The residue was dissolved in 200 milliliters of ethyl acetate and was washed with water (50 milliliters×3), 1 N HCl (50 milliliters×3) and with brine (50 milliliters×2). The organic layer was dried over an anhydrous sodium sulfate for 1 hour. After filtration, the solvent was removed by rotary evaporator. The residue was recrystallized from ethyl acetate. Yield: 5 grams (72%).

Step 4. Synthesis of Neopentyl Glycol Protected 4-(14'-hydroxy-3'-thia-1'-ketotetradecyl)-3-fluorophenylboronic acid (4).

An oven-dried, 500-milliliter, 3-necked, round-bottomed flask was charged with 5 grams (13 millimole) of 3 as prepared above. Addition of 100 milliliters of anhydrous dichloromethane produced a dispersion. While stirring, 1.42 grams (13.65 millimoles, 1.05 equivalents) of neopentylglycol was added to this dispersion. After few minutes a clear solution was obtained. The stirred reaction mixture was heated to reflux. A chiller and a Dean Stark apparatus were used to remove the dichloromethane-water azeotrope. The heating continued for about 3 hours.

At the end of reflux, the reaction mixture was allowed to cool to room temperature and the solvent was removed using a rotary evaporator. Anhydrous toluene (50 milliliters) was added to the residue and the toluene was removed using a rotary evaporator. This toluene treatment process was repeated once more. The residue was dissolved in 5 milliliters of dichlormethane, and hexane was added to this solution (with stirring) until cloudiness appeared (about 150 milliliters). The solution was kept in the freezer for recrystallizaton. After few hours the product crystallized and was isolated by filtration. Yield=5.13 grams (87%).

Step 5. Synthesis of Neopentyl Glycol Protected 4-(14'-bromo-3'-thia-1-ketotetradecyl)-3-fluorophenylboronic acid (5).

The reaction was carried out under $N_2$ atmosphere.

An oven-dried, 500-milliliter, 3-necked, round-bottomed flask was charged with 5.13 grams (11.33 millimole) of the neopentyl glycol protected boronic acid (4) and 50 milliliters of anhydrous dichloromethane under a nitrogen atmosphere. To this solution was added 7.52 grams (22.67 millimole, 2 equivalents) of carbon tetrabromide. The resulting solution was allowed to stir at 0° C. using an ice bath. A solution of 5.95 grams (22.67 millimole, 2 equivalents) of triphenylphosphine dissolved in 10 milliliters of anhydrous dichloromethane was added slowly to the reaction mixture using an addition funnel. The reaction mixture was stirred at 0° C. and was allowed to slowly warm to room temperature. Total reaction time was about 24 hours. At the end of the reaction 20 milliliters of methanol was added to the reaction mixture. After stirring for 1 hour, the solvent was removed by rotary evaporator. The residue was treated with 200 milliliters of diethyl ether and stirred for 30 minutes. The mixture was filtered and the solvent was removed under reduced pressure. The residue was given another ether treatment in the above manner and the solvent was removed. The resulting residue was flash chromatographed using hexane/ethyl acetate (98/2) as the solvent system. After removal of the solvent the product was isolated as an off-white solid. Yield=4.3 grams (74%).

Step 6. Synthesis of 4-(14'-trimethylammonium-3'-thia-1'-ketotetradecyl)-3-fluorophenylboronic acid chloride (6).

A 100-milliliter, round-bottomed flask was charged with 4.3 grams (8.3 millimole) of boronic acid derivative (5) and 40 milliliters of ethanol. To this solution was added 40 milliliters of aqueous trimethylamine solution (40%, Aldrich). The reaction mixture was stirred at 70° C. for 24 hours. After cooling to room temperature, the ethanol was removed by rotary evaporator. The remaining aqueous solution was cooled to 0° C. and 180 milliliters of 1 N HCl was added slowly into the stirring solution. If precipitation occurs, some methanol is added until a clear solution forms. After stirring for 5 hours, the solution (turbid) was extracted with chloroform (3×200 milliliters). Organic layers were collected and dried over sodium sulfate. The chloroform was evaporated and the residue was dissolved in methanol (20 milliliters). Sodium chloride solution (10% w/w, 200 milliliters) was added to the methanol solution and stirred for 1 hour. At this point, the organic solvent was removed using rotary evaporator and compound was extracted from aqueous solution with chloroform (3×200 milliliters). Organic layers were collected and dried over sodium sulfate. After filtration, the solvent was removed using rotary evaporator. The residue was added to 600 milliliters of ether and the mixture was kept in the freezer for 3 hours. The solvent was decanted to isolate the product. Yield=2 grams.

Example 2

Synthesis of 2,5-difluoro-4-(14'-hydroxy-3'-thia-1'-ketotetradecyl)phenylboronic acid (11)

The synthesis of Compound (11) is shown out schematically in FIG. 2. A detailed description of the procedure is provided below.

Step 1—Synthesis of 4-bromo-2,5-difluoroacetophenone (7)

Anhydrous aluminum chloride was mixed (5 grams, 37.5 millimoles, 2.4 equivalents) with 1-bromo-2,5 difluorobenzene in a dry, round-bottom flask blanketed with nitrogen and fitted with a condenser. The mixture was heated to 60° C. and acetyl chloride (1.7 milliliters, 23.3 millimole, 1.5 equivalents) was added by syringe. The wet yellow solid changed then into a scarlet solution and was heated at 90° C. for 1 hour. The reaction mixture was poured onto 38 grams of ice, HCl was added (3 milliliters, 37% concentration) and the mixture was extracted with ether. The crude material was dried over magnesium sulfate and evaporated down. The crude material was purified by column chromatography or distilled. The product (1.2 grams, 31%) was obtained as a yellow oil.

Step 2—Synthesis of Neopentyl Glycol Protected 4-acetyl-2,5-difluorofluorophenylboronic acid (8).

Dichloro [(1,1'-bis(diphenylphosphino)ferrocene] palladium (II) dichloromethane adduct (1.7 grams, 2.3 millimole, 5% mole) was added to a suspension of 4-bromo-2,5 difluoroacetophenone (7) (10.5 grams, 46.38 millimole, 1 equivalents), bis(neopentyl glycolato)diboron (12.57 grams, 55.65 millimole, 1.2 equivalents) and potassium acetate (13.66 grams, 139.13 millimole, 3 equivalents) in anhydrous DMSO (100 milliliters). The suspension was heated to 80° C. under nitrogen for 1 hour (*J. Org. Chem.* 60:7508 (1995)). After 1 hour, TLC showed full conversion of the starting material and the reaction mixture was allowed to cool down and extracted with toluene, washed three times with water and dried over magnesium sulfate. Flash column chromatography was used to purify the crude (4.2 grams, 32%).

Step 3—Synthesis of Neopentyl Glycol Protected 4-(2'-bromoacetyl)-2,5-difluorophenylboronic acid (9)

The boronic ester (8) (4.1 grams, 14.93 millimole, 1 equivalent) was dissolved in methylene chloride (50 milliliters) and cooled down to −10° C. Acetic acid (0.82 milliliters, 14.32 millimole, 1 equivalent) was added, followed by bromine (0.7 milliliters, 13.4 millimole, 0.9 equivalents) and the reaction was warmed up to room temperature. After stirring for two hours the reaction mixture was diluted with more methylene chloride and washed once with water and once with brine. The crude was dried over magnesium sulfate, evaporated down and used in the next step without further purification.

Step 4—Synthesis of Neopentyl Glycol Protected 2,5-difluoro-4-(14'-hydroxy-3'-thia-1'-ketotetradecyl)phenylboronic acid (10)

Crude Compound (9) (14.93 millimole) was dissolved in anhydrous methanol (50 milliliters) and nitrogen gas was bubbled into the solution for 20 minutes to degas the mixture. 11-mercaptoundecanol (3.1 grams, 14.93 millimole, 1 equivalent) was added to the reaction and the solution was allowed to stir under nitrogen for five minutes before adding anhydrous diisopropylamine (5.2 milliliters, 29.9 millimole, 2 equivalents). The reaction was left to stir under nitrogen overnight and the crude was worked up by evaporating the reaction mixture to dryness and re-dissolving it in a 10% mixture of THF in ethyl acetate (100 milliliters). This organic layer was then washed with 200 milliliters of water and the aqueous layer was separated and washed with three new fractions of the same THF/ethyl acetate mixture (100 milliliters each). The crude organic layers were combined, dried over magnesium sulfate and evaporated down. Flash chromatography was used to purify the crude and an off white solid was obtained (3.5 grams, 50%).

Step 5—Synthesis of 2,5-difluoro-4-(14'-hydroxy-3'-thia-1'-ketotetradecyl)phenylboronic acid (11).

De-protection of the neopentyl group in Compound (10) to give Compound (11) was carried out by dissolving Compound (10) in methanol and adding a few drops of HCl. After stirring for about an hour the crude product was concentrated on a rotary evaporator and the final compound was recrystallized from hot ethyl acetate.

Example 3

Synthesis of 2,5-difluoro-4-(13'-trimethylamonium-3'-thia-1'-ketotridecyl)phenyl (neopentyl glycolato) boron chloride (14)

The synthesis of Compound (14) is shown schematically in FIG. 3. A detailed description of the procedure is provided below.

Step 1—Synthesis of 10-bromodecyltrimethylammonium bromide 1,10-Dibromodecane (20 grams, 66.7 mmoles) and THF (100 milliliters) were placed in a 500-mL, three-necked flask. The solution was cooled to 0° C. with an ice-water bath. Anhydrous trimethylamine (3 grams, 50.8 mmoles) was added to the mixture by slowly bubbling trimethylamine gas for about 15 minutes. Then the reaction mixture was allowed to warm to room temperature and stirred at room temperature overnight. The solid material was filtered and washed with THF (5×30 milliliters). After drying in vacuo overnight, 12.5 grams (34.82 mmoles, 69% based on the amine used) of the product was obtained as a white solid.

Step 2—Synthesis of 10-mercaptodecyltrimethylammonium bromide

10-Bromodecyltrimethylammonium bromide (10 grams, 27.9 mmoles) in 50 mL of methanol was placed in a 250-milliliter, three-necked flask. The mixture was degassed vigorously by bubbling nitrogen for 30 minutes. Potassium thioacetate (3.8 grams, 33.5 mmoles, 1.2 equivalents) was added to the reaction mixture. The mixture was heated at 50° C. for 12 hours under nitrogen. The reaction mixture was cooled to 0° C. with an ice-water bath, degassed sodium hydroxide (50%, 2.7 grams, 33.5 mmoles, 1.2 equivalents) was added, and the mixture was stirred for 1 h at room temperature. The mixture was cooled to 0° C., and degassed concentrated hydrochloride acid was added dropwise to achieve pH 2. Degassed methanol (100 milliliters) was added to the reaction mixture, followed by the addition of 40 grams of magnesium sulfate. Magnesium sulfate was filtered off and washed with methanol. The methanol solution was concentrated to about 20 milliliters, and ether (300 milliliters) was added to the mixture. The flask was sealed and placed in a freezer. Product was crystallized out as a white solid. The product was filtered, washed with ether, and dried in vacuo. Product (7.5 grams, 24.0 mmoles, 86%) was obtained as a white hydroscopic solid.

Step 3—Synthesis of 2,5-difluoro-4-(13'-trimethylammonium-3'-thia-1'-ketotridecyl)fluorophenylboronic acid bromide 4-(2'-Bromoacetyl)-2,5-difluorophenyl (neopentyl glycolato) boron (Compound 9) (1 millimole) was dissolved in anhydrous methanol (10 milliliters) and nitrogen gas was bubbled into the solution for 20 minutes to degas the mixture. 10-mercaptodecyltrimethylammonium bromide (0.19 grams, 0.8 millimole, 0.8 equivalents) was added to the reaction and the solution was stirred under nitrogen for five minutes before adding anhydrous diisopropylamine (0.14 milliliters, 1 millimole, 1 equivalent). The reaction was stirred under nitrogen overnight and, after concentration on a rotary evaporator, purified by preparative reversed phase PLC.

Example 4

Synthesis of 4-(14'-trimethylammonium-3'-thia-1'-ketotetradecyl)phenylboronic acid chloride

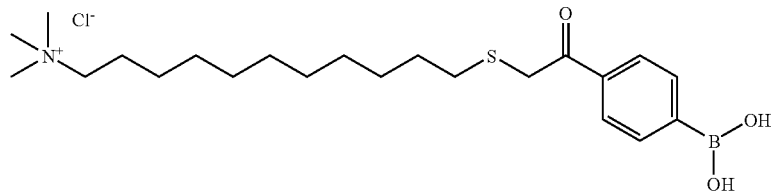

Step 1. Synthesis of 4-(2'-Bromoacetyl)phenylboronic acid.

An oven-dried, two liter, three-necked, round-bottomed flask was charged with 4-acetyl-phenylboronic acid (20 grams, 0.152 mole). While stirring, 175 ml of THF were added to the reaction mixture, followed by 700 ml of chloroform. To the resulting solution was added 5 ml of glacial acetic acid. A chloroform solution of bromine (prepared by dissolving 7 ml of bromine in 30 ml of chloroform) was added slowly to the reaction mixture at about 5° C. After the completion of the addition of bromine, the reaction mixture was allowed to warm to room temperature and stirred at room temperature for 16 hours. The solvent was removed by rotary evaporation and the residue was dissolved in 1 liter of ethyl acetate. The resulting solution was extracted with deionized water (3×200 ml) and brine (2×100 ml). The organic layer was dried over anhydrous sodium sulfate for 1 hour. The solution was then filtered and concentrated to about ⅓ of its volume. The resulting solution was kept in a freezer to crystallize the product. The solid was filtered to give an off white solid. Yield=16 grams Step 2. 4-(14'-hydroxy-3'-thia-1'-ketotetradecyl)phenylboronic acid.

A 500-ml, three-necked, round-bottomed flask was charged with 15 grams of 4-(2'-bromoacetyl)phenylboronic acid and 300 ml of anhydrous THF. While stirring under a nitrogen atmosphere, 12.26 grams of 11-mercaptoundecanol were added to the reaction mixture, followed by 32.35 ml of diisopropylethylamine. The reaction mixture was stirred under a nitrogen atmosphere for 48 hours. After removing the solvent by rotary evaporation, the residue was dissolved in 500 ml of ethyl acetate. The organic phase was washed with deionized water (2×200 ml), 1N HCl (3×200 ml), deionized water (200 ml), and brine (200 ml). The washed organic layer was then dried over anhydrous sodium sulfate for 15 minutes. The solution was filtered and concentrated to one fourth of its volume. While stirring, hexane was added slowly to this solution until permanent cloudiness appeared. The solution was kept in the freezer to crystallize the product. After filtration, the residue was dried under vacuum at room temperature yielding 17 grams of the product as an off-white solid.

Step 3. Synthesis of (neopentyl glycolato) 4-(14'-hydroxy-3'-thia-1'-ketotetradecyl)phenylboronate ester An oven-dried, 500 ml, 3-necked, round-bottomed, flask was charged with 5 grams of 4-(14'-hydroxy-3-thia-1-keto) tetradecyl phenylboronic acid and 100 ml of anhydrous dichloromethane. While stirring, 1 gram of neopentylglycol was added and the reaction mixture was heated to reflux with stirring. The heating continued for 3 hours with azeotropic distillation of water. The reaction mixture was allowed to cool to room temperature and the solvent was removed using a rotary evaporator. Anhydrous toluene (50 ml) was added to the residue and the toluene was removed using a rotary evaporator. This toluene treatment process was repeated once more. The residue was dissolved in 5 ml of dichloromethane and hexane was added to this solution (with stirring) until cloudiness appeared. The solution was kept in the freezer for recrystallizaton. The product was isolated by filtration, and upon drying, 4.8 grams of the compound was obtained as an off-white solid.

Step 4. Synthesis of (neopentyl glycolato) 4-(14'-bromo-3'-thia-1'-ketotetradecyl)phenylboronate ester.

An oven-dried, 500 ml, 3-necked, round-bottomed flask was charged with 5.13 grams of the (neopentyl glycolato) 4-(14'-hydroxy-3'-thia-1'-ketotetradecyl)phenylboronate ester and 50 ml of anhydrous dichloromethane. To this solution was added 7.52 grams of carbontetrabromide, and the resulting reaction mixture was allowed to stir at 0° C. using an ice bath. A solution of 5.95 grams of triphenylphosphine dissolved in 10 ml of anhydrous dichloromethane was added slowly to the reaction mixture using an addition funnel. The reaction mixture was stirred at 0° C. and then allowed to warm to room temperature slowly. After 16 hours, 20 ml of methanol was added to the reaction mixture. After stirring for 1 hour, the solvent was removed by rotary evaporator. The residue was treated with 200 ml of diethyl ether and stirred for 30 minutes. The mixture was filtered and the solvent was removed under reduced pressure. The residue was again treated with ether and the solvent was removed. The resulting residue was flash chromatographed using hexane/ethyl acetate (98/2). After removal of the solvent, the product was isolated as an off-white solid (yield=4.5 grams).

Step 5. 4-(14'-trimethylammonium-3'-thia-1'-keto-tetradecyl)phenylboronic acid chloride.

A 100 ml, round-bottomed, flask was charged with 500 mg of (neopentyl glycolato) 4-(14'-bromo-3'-thia-1'-ketotetradecyl)phenylboronate ester and 5 ml of ethanol. To this solution was added 5 ml of 40% aqueous solution of trimethylamine. The reaction mixture was stirred at 70° C. for 24 hours. After cooling to room temperature, the solvent was removed under reduced pressure. The residue was dissolved in 5 ml of methanol and 20 ml 2N HCl. After stirring for 24 hours, the solution was extracted with ethyl acetate (2×100 ml) to remove the neopentyl glycol. The aqueous solution was extracted with chloroform (3×50 ml). The chloroform extracts were combined and dried over $MgSO_4$. After filtration, the solvent was removed under reduced pressure and the residue was dried under vacuum to give 300 mg of a gummy solid.

Example 5

Synthesis of (Neopentyl Glycolato) 4-(14'-dimethylamino-3'-thia-1'-ketotetradecyl)phenylboronate ester

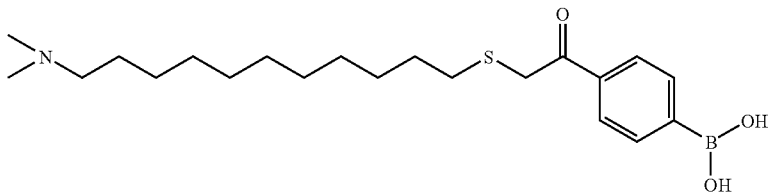

An oven-dried, 250 ml, 3-necked, round-bottomed flask was charged with 2.5 grams of the (neopentyl glycolato) 4-(14'-bromo-3'-thia-1'-keto)tetradecyl phenylboronate ester (prepared as described in Example 4, step 4) and 25 ml of anhydrous tetrahydrofuran (THF). To this mixture was added 8 ml of 2 M dimethylamine in THF. After stirring at room temperature for 48 hours, the solvent was removed under reduced pressure. The residue was stirred with 100 ml of 5% aqueous sodium bicarbonate solution for 1 hour and was then extracted with ethyl acetate (2×200 ml). After drying over anhydrous sodium sulfate, the solvent was removed under reduced pressure to yield 1.7 grams of the compound as a gummy solid.

Example 6

Synthesis of 4-{14'(3"-chlorotrimethylammium) dimethylpropylammonium-3'-thia-1'-ketotetradecyl}phenylboronic acid chloride

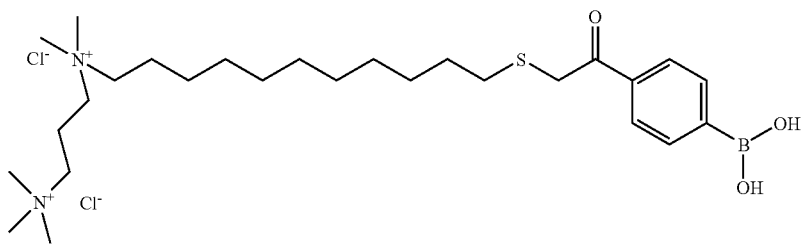

A 100 ml, round-bottomed, flask was charged with 700 mg of (neopentyl glycolato) 4-(14'-dimethylamino-3'-thia-1'-ketotetradecyl)phenylboronate ester (prepared as described in Example 5), 400 mg of 3-bromopropyltrimethylammonium bromide and 10 ml of ethanol. The reaction mixture was stirred at 70° C. for 24 hours. After cooling to room temperature, the solvent was removed under reduced pressure. The residue was dissolved in 5 ml of methanol and 40 ml 2 N HCl. After stirring for 24 hours, the solution was extracted with ethyl acetate (2×100 ml) to remove neopentyl glycol. The acidified aqueous solution was kept in the refrigerator. The precipitated solid was then isolated by removal of the solvent and dried under vacuum to yield 400 mg of a low melting solid.

Example 7

Synthesis of 4-(14'-sulfato-3'-thia-1'-ketotetradecyl)phenylboronic acid sodium salt

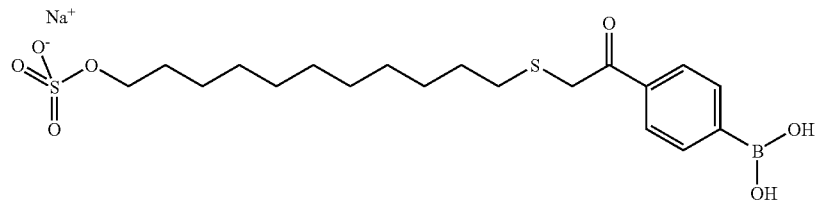

A 100 ml, round-bottomed flask was charged with 3 grams of 4-(14'-hydroxy-3'-thia-1'-ketotetradecyl)phenylboronic acid (prepared as described in Example 4, step 2) and 25 ml of N,N-dimethylformamide (DMF). To this solution was added 1.6 grams of sulfurtrioxide:DMF complex and the resulting reaction mixture was stirred at room temperature for 24 hours. To the reaction mixture was added a solution 2 grams of NaOH dissolved in 100 ml of water:methanol mixture (1:1) and stirred for 1 hour. The solvent was removed under pressure and the residue was treated with 100 ml of methanol. After stirring for 1 hour, the reaction mixture was filtered. The filtrate was rotary evaporated to dryness, yielding 1.5 grams of an off-white solid.

Example 8

Preparation of 4-(11'-hydroxyundecyl)carboxyphenylboronic acid

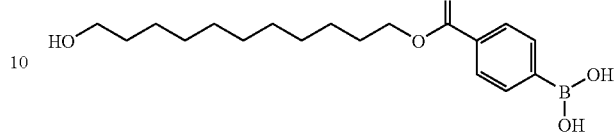

A mixture of 4-carboxyphenylboronic acid (1.0 grams), potassium hydrogen carbonate (2.01 g), 11-bromo-1-undecanol, and N,N-dimethylformamide (60 mL) was heated at 60° C. under a nitrogen atmosphere for 18 hours. After the heating period, the mixture was allowed to cool to room temperature. The mixture was then filtered and the filtrate was concentrated on a rotary evaporator. The concentrated filtrate was diluted with ethyl acetate (500 mL) and the ethyl acetate was washed successively with saturated aqueous sodium bicarbonate (3×300 mL), followed by saturated aqueous sodium chloride (300 mL). After drying over sodium sulfate, the ethyl acetate extract was concentrated on a rotary evaporator and dried under reduced pressure to afford 2.2 grams of the desired product as a light yellow viscous oil that solidified upon standing to a white powder.

The following compounds were synthesized using similar procedures:

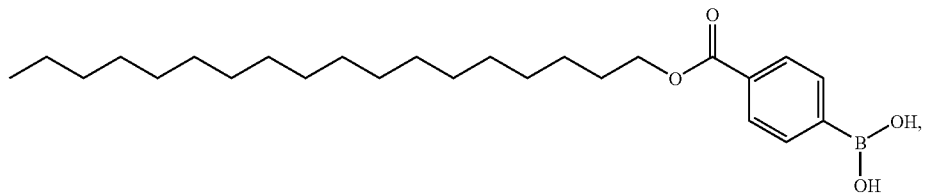

from 4-carboxyphenylboronic acid and iodooctadecane;

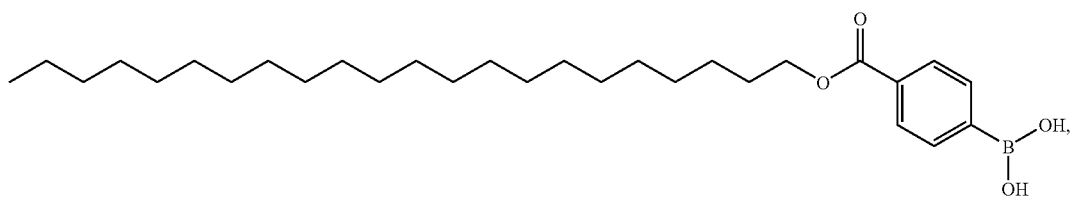

from 4-carboxyphenylboronic acid and docosyl methane sulfonate;

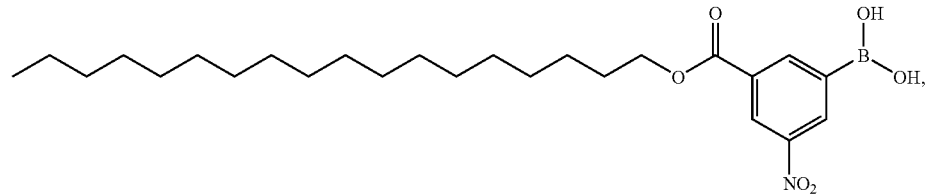

from bromooctadecane and (3-carboxy-5-nitrophenyl)boronic acid;

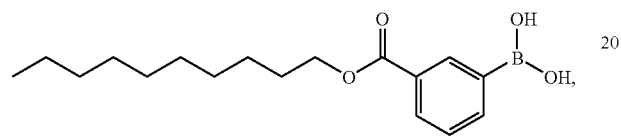

from 1-bromodecane and (3-carboxyphenyl)boronic acid;

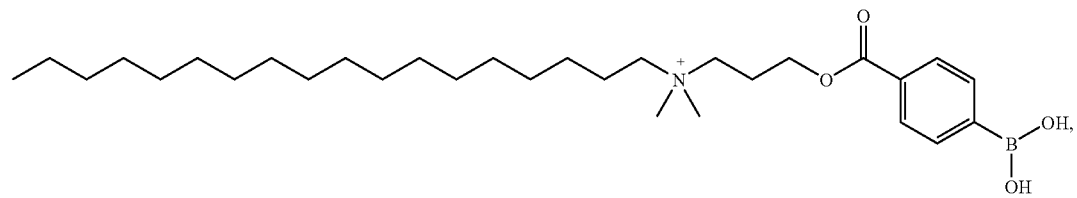

from 4-carboxyphenylboronic acid and (4-chloropropyl)dimethyloctadecylammonium bromide; and

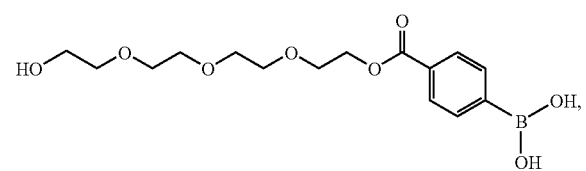

from 4-carboxyphenylboronic acid and pentethyleneglycol monotosylate.

Example 9

Synthesis of [4-(N,N-dioctadecylcarbamoyl)phenyl]boronic acid

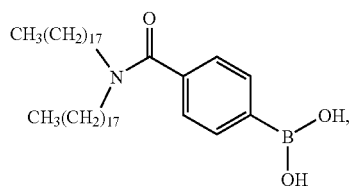

Step 1. Synthesis of 2-(4-carboxyphenyl)-1,3-dioxa-2-borinane.

A mixture of 4-carboxyphenylboronic acid (5.0 grams) and 1,3-propanediol (2.5 grams) in toluene (300 mL) was refluxed with a Dean-Stark apparatus for 6 hours. After the heating period the reaction solution was concentrated on a rotary evaporator and dried under reduced pressure to afford 6.39 grams of the desired product as a white solid.

Step 2. Synthesis of 2-(4-carbonylchloride)-1,3-dioxa-2-borinane.

To a solution of the above propane diol protected 4-carboxyphenylboronic acid (1.0 grams) in chloroform (5 mL) was added thionyl chloride (3.0 mL) and dimethylformamide (100 microliters). The solution was heated to reflux for 2 hours. After the heating period, the reaction solution was allowed to cool to room temperature and was concentrated on a rotary evaporator under reduced pressure. To the residue was added chloroform (8 mL) and the resulting solution was concentrated on a rotary evaporator. The addition of chloroform (8 mL) and the concentrating of the solution was repeated twice more. The crude material was dried under vacuum to afford 1.09 grams of the desired product as an off-white solid.

Step 3. Synthesis of [4-(N,N-dioctadecylcarbamoyl)phenyl]boronic acid.

To a solution of 2-(4-carbonylchloride)-1,3-dioxa-2-borinane (0.8 grams) in chloroform (30 mL) under nitrogen was added dioctadecylamine (1.93 grams), triethylamine (1.0 mL), and chloroform (10 mL). The reaction mixture was allowed to stir overnight, afterwhich it was diluted with chloroform (200 mL). The chloroform solution was washed in a separatory funnel successively with the following aqueous solutions: 10% HCl (3×100 mL), saturated sodium bicarbonate (3×100 mL), and saturated sodium chloride (100 mL). The chloroform extract was dried over sodium sulfate. 2.41 grams of crude material was isolated after filtration and concentration on a rotary evaporator under reduced pressure. The desired product was purified via column chromatography over silica gel using a mixture of ethyl acetate and hexane as eluent.

Example 10

Synthesis of 4-(13'-carboxy-3'-thia-1'-ketotridecyl) phenylboronic acid

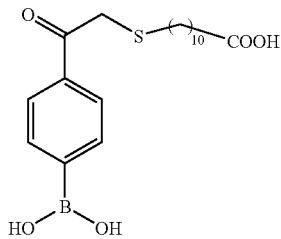

A 100-mL, three-necked flask was charged with 4-(2'-bromoacetyl)phenyl boronic acid (0.95 g, 3.91 mmol) and 20 mL THF. The mixture was degassed by bubbling nitrogen through the reaction mixture for about 20 minutes. 11-Mercaptoundecanoic acid (0.9 g, 4.1 mmol) was added to the reaction mixture with stirring under nitrogen. Diisopropylethylamine (1.52 g, 2.05 mL, 11.8 mmol) was then added via a syringe over 5 minutes. The reaction mixture was stirred for 72 hours under nitrogen at room temperature. The solvent was removed in vacuo, and the residue was partitioned between ethyl acetate (100 mL) and water (100 mL). The organic extract was washed with 1 N hydrochloric acid (3×100 mL), water (100 mL) and brine (100 mL). The organic extract was dried over magnesium sulfate and then filtered. The filtrate was then concentrated in vacuo. The residue was dissolved in about 25 mL of hot ethyl acetate. When the mixture was cooled to room temperature, it was placed in a freezer. Product crystallized from the solution. The white crystalline material was filtered, washed with cold ethyl acetate, and dried in vacuo. 0.93 g (2.45 mmol) of the pure product was obtained. Yield: 62.5%.

Example 11

Synthesis of Poly(N-diethanolaminopropyl)acrylamide (17)

The synthesis of Polymer (17) is shown out schematically in FIG. 4. A detailed description of the procedure is provided below.

Step 1: Synthesis of (N-diethanolaminopropyl)acrylamide (16)

A 2-liter, 3-necked, round-bottomed flask with overhead stirring was charged with 80.08 grams of N-(3-aminopropyl) diethanolamine and 200 milliliters of deionized water. To this mixture was added 3.18 grams of K$_2$CO3 and the resulting solution was cooled to less than 5° C. with an ice bath. 130 milliliters of dichloromethane with vigorous stirring. This was followed by the addition of 45.0 milliliters of acryloylchloride (about 1.1 equivalents relative to amine) in 50 milliliters of dichloromethane.

A 50% aqueous solution of KOH was prepared by dissolving 20.58 grams of KOH (about 0.74 equivalents with respect to amine) in 25 milliliters of deionized water. About half of the acryloylchloride solution over 30 to 45 minutes until the pH between 7 and 8. The KOH solution and acryloylchloride solution were then added dropwise simultaneously, keeping the pH between 8 and 9. The reaction was stirred overnight and allowed to warm to room temperature. The next day, the aqueous layer was separated from the organic layer, which was discarded.

The water was removed at 30° C. to 35° C. using a rotary evaporator until orange/brown oil remained. The KCl was filtered during this procedure. The oil was then dissolved in 500 milliliters of methanol and stirred for 20 minutes. The remaining KCl was then filtered. The methanol then removed in vacuo, leaving orange/brown oil. This monomer (16) (126.7 grams) is used directly for polymerization without further purification.

Step 2: Synthesis of Poly(N-diethanolaminopropyl)acrylamide (17)

126.7 grams of Compound (16) was dissolved in 750 milliliters of deionized water (about 15% w/v) in a 1-liter, round-bottomed flask. To this solution was added 0.4942 grams (about 0.5 wt %) of V-50 initiator as a solid. The vessel was purged with nitrogen for 30 minutes to obtain a clear, golden-colored and homogeneous solution. The mixture was heated at 65° C. After about 18 hours of heating, a second batch of V50 (0.2761 grams dissolved in 3.0 milliliters of deionized water) was added to the reaction. After about 42 hours of heating, a third batch of V50 (0.2644 grams dissolved in 3.0 milliliters of deionized water) was added. After another 72 hours, the heat was removed and the reaction mixture was allowed to cool to room temperature.

The material was dialyzed (molecular weight cut off 3.5 K) over 24 hours with a water change after 16 hours. The purified polymer was then dried in a forced air oven at 50° C. for 30 hours. An orange and tacky film was obtained and was then redissolved in 300 milliliters of methanol. The solvent was removed in vacuo to yield an oil, which was then precipitated into 3 liters of ether. The gummy mass was then vacuum dried at about 35° C. to 40° C. for 16 hours. The final yield of (17) was 50 grams of a grindable, yellow solid (50% recovery).

Example 12

Synthesis of Boronate Ester Functionalized Polymers

A. Synthesis of poly(N-diethanolaminopropyl)acrylamide conjugated with 4-(14'-trimethylammonium-3'-thia-1'-ketotetradecyl)-3-fluorophenylboronic acid bromide (Polymer: Boronic acid 1:1) (Polymer 1)

178 milligrams of poly(N-diethanolaminopropyl)acrylamide and 5 milliliters of anhydrous methanol were combined in a 50 milliliter round-bottomed flask. The reaction mixture was allowed to stir until a clear solution was obtained. To this solution was added 390 milligrams of 4-(14'-trimethylammonium-3'-thia-1'-ketotetradecyl)-3-fluorophenylboronic acid bromide. The homogeneous solution was stirred at 40° C. for 1 hour. The solvent was removed under reduced pressure. The residue was dissolved in 5 milliliters of anhydrous dimethylsulfoxide and the resulting solution was precipitated with anhydrous chloroform. This dissolution and precipitation procedure was repeated and the residue dried under vacuum at 35° C. to yield an off white solid. Yield was 488 milligrams.

B. Synthesis of poly(N-diethanolaminopropyl)acrylamide conjugated with 4-(14'-trimethylammonium-3'-thia-1'-ketotetradecyl)-3-fluorophenylboronic acid bromide(Polymer: Boronic acid, 1:0.5). (Polymer 2)

277 milligrams of poly(N-diethanolaminopropyl)acrylamide and 5 milliliters of anhydrous methanol were combined in a 50 milliliter round-bottomed flask. The reaction mixture was allowed to stir until a clear solution was obtained. To this solution was added 253 milligrams of 4-(14'-trimethylammonium-3'-thia-1'-ketotetradecyl)-3-fluorophenylboronic acid bromide. The homogeneous solution was stirred at 40° C. for 1 hour. The solvent was removed under reduced pressure. The residue was dissolved in 5 milliliters of anhydrous dimethylsulfoxide and the resulting solution was precipitated with anhydrous chloroform. This dissolution and precipitation procedure was repeated and the residue dried under vacuum at 35° C. to yield an off white solid. Yield was 519 milligrams.

C. Synthesis of poly(N-diethanolaminopropyl)acrylamide conjugated with 4-(14'-trimethylammonium-3'-thia-1'-ketotetradecyl)phenylboronic acid bromide(Polymer: Boronic acid, 1:1). (Polymer 3)

209 milligrams of poly(N-diethanolaminopropyl)acrylamide and 5 milliliters of anhydrous methanol were combined in a 50 milliliter round-bottomed flask. The reaction mixture was allowed to stir until a clear solution was obtained. To this solution was added 450 milligrams of 4-(14'-trimethylammonium-3'-thia-1'-ketotetradecyl)phenylboronic acid bromide. The homogeneous solution was stirred at 40° C. for 1 hour. The solvent was removed under reduced pressure. The residue was dissolved in 5 milliliters of anhydrous dimethylsulfoxide and the resulting solution was precipitated with anhydrous chloroform. This dissolution and precipitation procedure was repeated and the residue dried under vacuum at 35° C. to yield an off white solid. Yield was 600 milligrams.

D. Synthesis of Poly(N-diethanolaminopropyl)acrylamide conjugated with 4-(13'-trimethylammonium-3'-thia-1'-ketotridecyl)-3-fluorophenylboronic acid bromide (Polymer: Boronic acid, 1:0.5). (Polymer 4)

187 milligrams of poly(N-diethanolaminopropyl)acrylamide and 5 milliliters of anhydrous methanol were combined in a 50 milliliter round-bottomed flask. The reaction mixture was allowed to stir until a clear solution was obtained. To this solution was added 253 milligrams of 4-(13'-trimethylammonium-3'-thia-1'-ketotridecyl)-3-fluorophenylboronic acid bromide. The homogeneous solution was stirred at 40° C. for 1 hour. The solvent was removed under reduced pressure. The residue was dissolved in 5 milliliters of anhydrous dimethylsulfoxide and the resulting solution was precipitated with anhydrous chloroform. This dissolution and precipitation procedure was repeated and the residue dried under vacuum at 35° C. to yield an off white solid. Yield was 177 milligrams.

E. Synthesis of Poly(N-diethanolaminopropyl)acrylamide conjugated with 4-(14'-hydroxy-3'-thia-1'-ketotetradecyl)-3-fluorophenylboronic acid (Polymer: Boronic acid 1:1) (Polymer 5)

64 milligrams of poly(N-diethanolaminopropyl)acrylamide and 5 milliliters of anhydrous methanol were combined in a 50 milliliters round-bottomed flask. The reaction mixture was allowed to stir until a clear solution was obtained. To this solution was added 113 milligrams of 4-(14'-hydroxy-3'-thia-1'-ketotetradecyl)-3-fluorophenylboronic acid. The homogeneous solution was stirred at 40° C. for 1 hour. The solvent was removed under reduced pressure. The residue was dissolved in 5 milliliters of anhydrous dimethylsulfoxide and the resulting solution was precipitated with anhydrous chloroform. This dissolution and precipitation procedure was repeated and the residue dried under vacuum at 35° C. to yield an off white solid. Yield was 90 milligrams.

F. Synthesis of Poly(N-diethanolaminopropyl)acrylamide conjugated with 4-(14'-hydroxy-3'-thia-1'-ketotetradecyl)phenylboronic acid (Polymer: Boronic acid 1:1) (Polymer 6)

243 milligrams of poly(N-diethanolaminopropyl)acrylamide and 5 milliliters of anhydrous methanol were combined in a 50 milliliters round-bottomed flask. The reaction mixture was allowed to stir until a clear solution was obtained. To this solution was added 408 milligrams of 4-(14'-hydroxy-3'-thia-1'-ketotetradecyl)phenylboronic acid. The homogeneous solution was stirred at 40° C. for 1 hour. The solvent was removed under reduced pressure. The residue was dissolved in 5 milliliters of anhydrous dimethylsulfoxide and the resulting solution was precipitated with anhydrous chloroform. This dissolution and precipitation procedure was repeated and the residue dried under vacuum at 35° C. to yield an off white solid. Yield was 400 milligrams.

G. Synthesis of Poly(N-diethanolaminopropyl)acrylamide conjugated with 4-(14'-hydroxy-3'-thia-1'-ketotetradecyl)phenylboronic acid (Polymer: Boronic acid 1:0.5) (Polymer 7)

478 milligrams of poly(N-diethanolaminopropyl)acrylamide and 5 milliliters of anhydrous methanol were combined in a 50 milliliter round-bottomed flask . The reaction mixture was allowed to stir until a clear solution was obtained. To this solution was added 402 milligrams of 4-(14'-hydroxy-3'-thia-1'-ketotetradecyl)phenylboronic acid. The homogeneous solution was stirred at 40° C. for 1 hour. The solvent was removed under reduced pressure. The residue was dissolved in 5 milliliters of anhydrous dimethylsulfoxide and the resulting solution was precipitated from anhydrous chloroform. This dissolution and precipitation procedure was repeated and the residue dried under vacuum at 35° C. to yield an off white solid. Yield was 600 milligrams.

H. Synthesis of Poly{N-(2-hydroxy)ethyl ethylenimine) conjugated with 4-(14'-hydroxy-3'-thia-1'-ketotetradecyl) phenylboronic acid (Polymer 8)

To a solution of 196 mg of poly{N-(2-hydroxy)ethyl ethylenimine} dissolved in 10 milliliters of methanol was added a solution of 1 g of 4-(14'-hydroxy-3'-thia-1'-ketotetradecyl) phenylboronic acid dissolved in 20 milliliter of methanol. The solution was stirred at 40° C. for 30 minutes. After removing methanol under reduced pressure, the residue was extracted with 100 milliliter of warm tetrahydrofuran for 45 minutes. This process was repeated twice. After filtration the residue was dried under reduced pressure at 35° C. yielding 200 mg of the product as a pale yellow solid.

I. Synthesis of Poly{N,N-di(1,2-dihydroxy)propyl diallylamine} conjugated with 4-(14'-hydroxy-3'-thia-1'-ketotetradecyl)phenylboronic acid (Polymer 9)

To a solution of 366 mg of poly{N,N-di(1,2-dihydroxy) propyl diallylamine} dissolved in 25 milliliters of methanol was added a solution of 1 g of 4-(14'-hydroxy-3'-thia-1'-ketotetradecyl)phenylboronic acid dissolved in 20 milliliter of methanol. The solution was stirred at 40° C. for 30 minutes. After removing methanol under reduced pressure, the residue was extracted with 100 milliliter of warm tetrahydrofuran for 45 minutes followed by 100 milliliter of warm ethyl acetate for 30 minutes. After filtration the residue was dried under reduced pressure at 35° C. yielding 250 mg of the product as a pale yellow solid.

Example 13

Polymers of the Present Invention Inhibit Lipase Activity In Vitro

An in vitro assay of pancreatic lipase activity was used to measure the efficacy of lipase inhibitory compounds. Porcine pancreatic lipase (23 units/milliliters) was incubated for 4 hours at 37° C. with 72 mM triglyceride (as an olive oil/gum arabic emulsion) in 5.5 milliliters of a 300 mM BES buffer, pH 7.0, containing 10 mM $CaCl_2$, 109 mM NaCl, and 8 mM sodium taurocholate. The reaction was stopped by acidification with HCl and the lipids were extracted by the disclosed in Folch, et al., *J. Biol. Chem.* 226:497 (1957) prior to analysis by HPLC. An aliquot of the chloroform layer was evaporated and reconstituted in hexane, and the sample was analyzed on a Waters Alliance 2690 HPLC with a Sedex 55 Evaporative Light Scattering detector utilizing a YMC PVA Sil 3×50 millimeter column. The mobile phase consisted of hexane and methyl t-butyl ether delivered in a linear gradient at a flow rate of 0.5 milliliters/minute. External standards were utilized for quantitation of triglycerides, diglycerides, and fatty acids, and the percent lipolysis was determined. For evaluation of lipase inhibitor efficacy, compounds were dissolved in DMSO or another appropriate solvent and added directly to the assay mixture prior to incubation. Inhibition was determined relative to a control incubation and $IC_{50}$ values were calculated from a plot of % inhibition vs. inhibitor concentration. $IC_{50}$ values are shown in the Table. As can be seen, the polymes tested are effective inhibitors of lipase.

Example 14

Polymers of the Present Invention Inhibit Lipolysis In Vivo

Compounds were evaluated in rats to determine their in vivo potency in inhibiting fat absorption through lipase inhibition. Rats were acclimated to the facility for approximately 1 week in individual wire-bottom cages and provided a standard chow diet and water ad libitum. Rats were then randomly assigned to groups of 4. They were gavaged at (7–8 AM) with 4 milliliters olive oil emulsified with gum arabic, with or without drug following an 18 hour fast. Test compounds were dissolved in DMSO or deionized water. Drug solutions were mixed thoroughly in the olive oil emulsion just prior to administration. After 8 hours, rats were euthanized with $CO_2$ and the intestines were removed. The intestinal contents were harvested from the lower half of the small intestine and the cecum. Contents were placed in separate, pre-weighed, 15 milliliter conical screw cap tubes in a (dry ice/alcohol bath) to maintain freezing temperature until the final freeze of all samples. Samples were stored at −80° C. until lyophilization.

Samples were freeze-dried and ground, then analyzed for triglyceride and fatty acid.

A 20 milligram aliquot of each sample was weighed and transferred to a 15 milliliter conical tube. 3 milliliters of hexane were added to each tube, which were capped and vortexed for 15 seconds at high speed. 3 milliliters of 1 N HCl were added and the samples were then subjected to wrist-action shaking for 1 hour. Samples were then centrifuged for 5 minutes at 3500 rpm and the hexane layer was collected. An aliquot of the hexane layer was diluted in hexane and analyzed for triglyceride, diglyceride and fatty acid by HPLC as described above.

The data was expressed as follows. The milligrams of intestinal contents that was extracted and the total number of milligrams collected were recorded. The milligrams/milliliters values obtained from the HPLC analysis were entered. The individual lipid components were calculated and expressed as total milligrams recovered. Dose units are expressed as the milligrams of drug per gram of oil administered to each rat. The $ED_{50}$'s were determined by extrapolating the dose value at half the maximum obtainable triglyceride recoverable in the assay. The results are shown in the Table. As can be seen, the polymers are effective in inhibiting lipolysis in vivo.

THE TABLE

Inhibition of in vitro and in vivo lipolysis

| Polymer Compound | In Vitro Pancreatic Lipase Assay $IC_{50}$ (μg/g fat) or estimate | In Vivo Infusion Assay in Rats $ED_{50}$ (mg/g fat) or estimate | In Vivo Infusion Assay in Rats $Ed_{50}$ (mg/kg body wt) or estimate |
|---|---|---|---|
| Polymer 1 | 5.2 | 3 | 22.5 |
| Polymer 2 | 5.3 | 4.5 | 33.8 |
| Polymer 3 | 16.0 | 20 | 150 |
| Polymer 4 | not assayed | not assayed | not assayed |
| Polymer 5 | 4.5 | 50 | 375 |
| Polymer 6 | 15 | 36 | 270 |
| Polymer 7 | 10 | not assayed | not assayed |

While this invention has been particularly shown and described with references to preferred embodiments thereof, it will be understood by those skilled in the art that various changes in form and details may be made therein without departing from the scope of the invention encompassed by the appended claims.

What is claimed is:

1. A polymer comprising one or more pendent groups represented by a structural formula selected from:

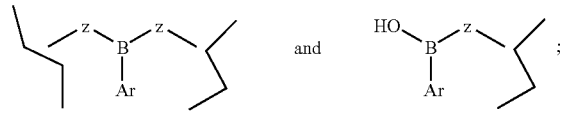

or a pharmaceutically acceptable salt of said polymer, wherein Ar is a substituted or unsubstituted aryl group; and each Z is —NH—, —O— or —S— and is independently selected, and wherein at least one is —NH— or —S—.

2. A polymer comprising one or more pendent aryl boronate ester groups represented by structural formula:

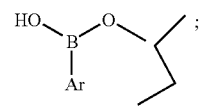

or a pharmaceutically acceptable salt of said polymer, wherein Ar is a substituted or unsubstituted aryl group.

3. A polymer comprising one or more pendent groups represented by a structural formula selected from:

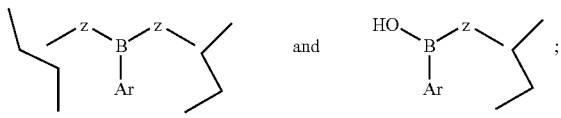

or a pharmaceutically acceptable salt of said polymer, each Z is —NH—, —O— or —S— and is independently selected, and wherein Ar is an aryl group substituted with at least one electron withdrawing group.

4. The polymer of claim 3, wherein Z is —O—.

5. The polymer of claim 4, wherein the pendent aryl boronate ester groups are represented by a structural formula selected from:

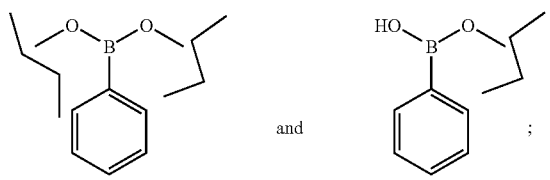

wherein the phenyl ring is substituted with one or more electron withdrawing groups.

6. The polymer of claim 5 wherein the pendent phenyl boronate ester groups are represented by a structural formula selected from:

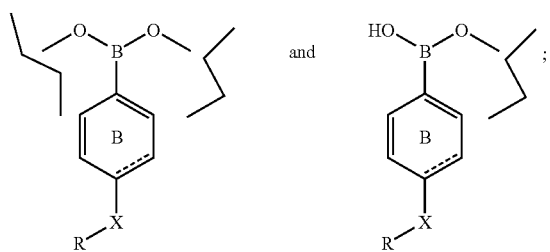

wherein:
X is an electron withdrawing group;
R is a substituted or unsubstituted straight chained hydrocarbyl group optionally containing one or more ether, thioether, phenylene, amine or ammonium linkage; and
the Phenyl Ring is substituted or unsubstituted.

7. The polymer of claim 6 wherein X is —CHD-, —CD$_2$-, —COO—, —CONH—, —CO—, —S(O)—, —S(O)$_2$O— or —SO$_2$—; the Phenyl Ring is optionally substituted with one or more electron withdrawing groups; D is a halogen; and R is a straight chained hydrocarbyl group with an ether or thioether linkage and is optionally substituted at the terminal position with an amine, halogen, —CF$_3$, thiol, ammonium, alcohol, —COOH, —SO$_3$H, —OSO$_3$H or phosphonium group.

8. The polymer of claim 7 wherein X is —CHD-, —CD$_2$-, —COO—, —CONH—, —CO— or —SO$_2$—.

9. The polymer of claim 6 wherein X is —CHD-, —CD$_2$-, —COO—, —CONH—, —CO— or —SO$_2$—; the Phenyl Ring is optionally substituted with one or more electron withdrawing groups; D is a halogen; and R is a straight chained hydrocarbyl group with an ether or thioether linkage and is substituted at the terminal position with —[NH—(CH$_2$)$_q$]$_r$—NH$_2$), wherein q is an integer from 2 to about 10 and r is an integer from 1 to about 5, provided that one or more of the secondary amines in —[NH—(CH$_2$)$_q$]$_r$—NH$_2$) are optionally N-alkylated or N,N-dialkylated and the primary amine in —[NH—(CH$_2$)$_q$]$_r$—NH$_2$) is optionally N-alkylated, N,N-dialkylated or N,N,N-trialkylated.

10. The polymer of claim 6, wherein X is —CO—.

11. The polymer of claim 10 wherein the Phenyl Ring is optionally substituted with one or more additional electron withdrawing groups; R is a straight chained hydrocarbyl group optionally comprising an ether or thioether linkage; and R is substituted at the terminal position with an amine, halogen, —CF$_3$, thiol, ammonium group, alcohol, —COOH, —SO$_3$H, —OSO$_3$H or phosphonium group.

12. The polymer of claim 11 wherein R is a straight chained hydrocarbyl group comprising an ether or thioether linkage and substituted at the terminal position with an ammonium group.

13. The polymer of claim 11 wherein R is a straight chained hydrocarbyl group comprising an ether or thioether linkage and substituted at the terminal position with a trialkyl ammonium group.

14. The polymer of claim 11 wherein R is a straight chained hydrocarbyl group comprising an ether or thioether linkage and substituted at the terminal position with a trimethyl ammonium group.

15. The polymer of claim 10 wherein the Phenyl Ring is optionally substituted with one or more additional electron withdrawing groups; R is a straight chained hydrocarbyl group with an ammonium linkage and optionally substituted at the terminal position with an amine, halogen, —CF$_3$, thiol, ammonium group, alcohol, —COOH, —SO$_3$H, —OSO$_3$H or phosphonium group.

16. The polymer of claim 10 wherein the Phenyl Ring is optionally substituted with one or more additional electron withdrawing groups; R is a straight chained hydrocarbyl group with an ammonium linkage.

17. The polymer of claim 10 wherein the Phenyl Ring is optionally substituted with one or more additional electron withdrawing groups; R is a straight chained hydrocarbyl group substituted at the terminal position with an amine, halogen, —CF$_3$, thiol, ammonium group, alcohol, —COOH, —SO$_3$H, —OSO$_3$H or phosphonium group.

18. The polymer of claim 17 wherein R is a straight chained hydrocarbyl group substituted at the terminal position with an ammonium group.

19. The polymer of claim 17 wherein R is a straight chained hydrocarbyl group substituted at the terminal position with a trialkyl ammonium group.

20. The polymer of claim 6 wherein —XR is —C(O)CH$_2$—O[—(CH$_2$)pO]m-(CH$_2$)p-Y or —C(O)CH$_2$—S[—(CH$_2$)pO]m-(CH$_2$)p-Y, p is 2 or 3, m is an integer from 1–5 and Y is an ammonium group.

21. The polymer of claim 10 wherein the phenyl boronate ester groups are represented by the following structural formula:

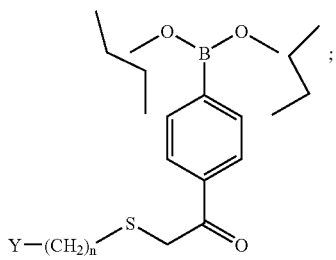

wherein Y is an ammonium group and n is an integer from 3 to about 30.

22. The polymer of claim 21 wherein Y is a trialkylammonium group.

23. The polymer of claim 22 wherein Y a trimethylammonium group.

24. The polymer of claim 10 wherein the phenyl boronate group is connected directly to the polymer backbone.

25. The polymer of claim 23 wherein the polymer is polyvinyl alcohol or a polysaccharide.

26. The polymer of claim 10 wherein the polymer is a fat-binding polymer.

27. The polymer of claim 26 wherein the polymer is cationic.

28. The polymer of claim 26 wherein the polymer is a synthetic polyamine.

29. The polymer of claim 3, wherein the polymer comprises a phenyl boronate functionalized repeat unit, said repeat unit comprising a moiety W represented by a structural formula selected from:

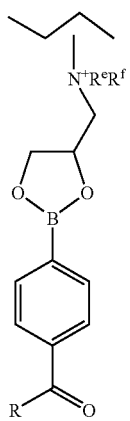
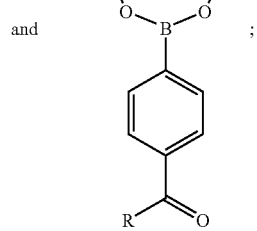

$R^e$ and $R^f$ are independently —H, a substituted or unsubstituted alkyl group or a substituted or unsubstituted benzyl group;

R is a substituted or unsubstituted straight chained hydrocarbyl group optionally containing one or more ether, thioether, phenylene, amine or ammonium linkages; and the Phenyl Ring is substituted or unsubstituted,
or a pharmaceutically acceptable salt of said polymer.

30. The polymer of claim 3, wherein the polymer comprises a phenyl boronate functionalized repeat unit, said repeat unit comprising a moiety W represented a structural formula selected from:

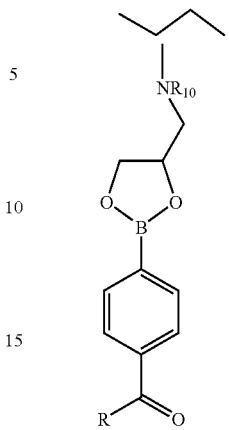
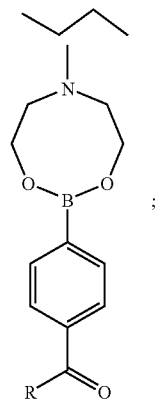

$R_{10}$ is —H, a substituted or unsubstituted alkyl group or a substituted or unsubstituted benzyl group;

R is a substituted or unsubstituted straight chained hydrocarbyl group optionally containing one or more ether, thioether, phenylene, amine or ammonium linkages; and the Phenyl Ring is substituted or unsubstituted, and
pharmaceutically acceptable salts of said polymer.

31. The polymer of claim 30 wherein $R_{10}$ is —H.

32. The polymer of claim 31 wherein the Phenyl Ring is optionally substituted with one or more additional electron withdrawing groups and R is a straight chained hydrocarbyl group comprising an ether or thioether linkage and substituted at the terminal position with an amine, halogen, —$CF_3$, thiol, ammonium group, alcohol, —COOH, —$SO_3H$, —$OSO_3H$ or phosphonium group.

33. The polymer of claim 32 wherein R is a straight chained hydrocarbyl group comprising an ether or thioether linkage and substituted at the terminal position with an ammonium group.

34. The polymer of claim 32 wherein R is a straight chained hydrocarbyl group comprising an ether or thioether linkage and substituted at the terminal position with a trialkylammonium group.

35. The polymer of claim 32 wherein R is a straight chained hydrocarbyl group comprising an ether or thioether linkage and substituted at the terminal position with a trimethylammonium group.

36. The polymer of claim 31 wherein R is a straight chained hydrocarbyl group comprising an ammonium linkage.

37. The polymer of claim 31 wherein the boron functionalized repeat unit is represented by the following structural formula:

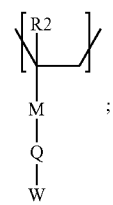

wherein:

M is a covalent bond, —CH₂—, 1,4-phenylene, —C(O)O—, —C(O)NR1, —C(O)—, —O—, —NR1-, —CH₂NR1-, —CH₂O—, —N⁺R1R1- or —CH₂N⁺R1R1-;

Q is a covalent bond or an inert spacer group;

Each R1 is independently —H, an aliphatic group or a substituted aliphatic group; and $R_2$ is —H or a C1–C6 alkyl group.

38. The polymer of claim 37 wherein M is a covalent bond, —CH₂—, 1,4-phenylene, —C(O)O—, —C(O)NR1, —C(O)—, —O—, —NR1-, —CH₂NR1- or —CH₂O—.

39. The polymer of claim 37 wherein the repeat unit is represented by the following structural formula:

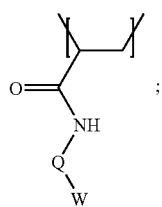

wherein Q is a hydrocarbyl group optionally containing a linking heteroatom functional group.

40. The polymer of claim 39 wherein Q is a C1 to C30 alkylene group.

41. The polymer of claim 40 wherein R is —CH₂—S—(CH₂)n-Y, n is an integer from about 6 to about 30 and Y is an ammonium group.

42. The polymer of claim 41 wherein Y is a trialkylammonium group.

43. The polymer of claim 41 wherein Y is a trimethylammonium group.

44. The polymer of claim 10 wherein the polymer is crosslinked.

45. The polymer of claim 10 wherein the polymer comprises hydrophobic groups.

46. The polymer of claim 10 wherein the polymer is a copolymer comprising a hydrophobic comonomer.

47. The polymer of claim 3, wherein the polymer comprises repeat units represented by the following structural formula:

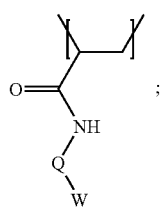

wherein Q is a C1 to C15 alkylene group and W is represented by the following structural formula:

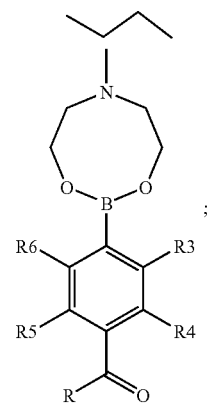

wherein R3–R6 are independently —H or —F, R is —CH₂—S—(CH₂)n-Y; Y is an ammonium group; and n is an integer from about 1 to about 15;

or a pharmaceutically acceptable salt of said polymer.

48. The polymer of claim 47 wherein Y is a trialkylammonium group.

49. The polymer of claim 47 wherein Y is a trimethylammonium group.

50. The polymer of claim 49 wherein R3, R6 and R5 are —H and R4 is —F.

51. A method of inhibiting the uptake of fat in the gastrointestinal tract of a subject in need of such treatment, said method comprising the step of administering to the subject an effective amount of a polymer comprising one or more groups selected from pendent aryl boronate ester groups, pendent aryl boronamide groups and aryl boronate thioester groups, wherein the groups are represented by a structural formula selected from:

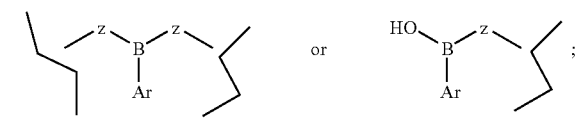

or a pharmaceutically acceptable salt of said polymer, wherein Ar is a substituted or unsubstituted aryl group; and each Z is —O—, —NH— or —S— and is independently selected.

52. The method of claim 51 wherein the subject is being treated for obesity.

53. The method of claim 52 wherein each Z is —O—.

54. A method of inhibiting the uptake of fat in the gastrointestinal tract of a subject in need of such treatment, said method comprising the step of administering to the subject an effective amount of a polymer comprising one or more pendent phenyl boronate ester groups represented by a structural formula selected from:

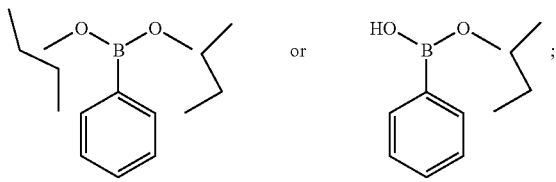

wherein the Phenyl Ring is substituted or unsubstituted, or a pharmaceutically acceptable salt of said polymer.

55. The method of claim 54 wherein the subject is being treated for obesity.

56. The method of claim 55 wherein the Phenyl Ring is substituted with one or more electron withdrawing groups.

57. The method of claim 56 wherein the pendent phenyl boronate ester groups are represented by a structural formula selected from:

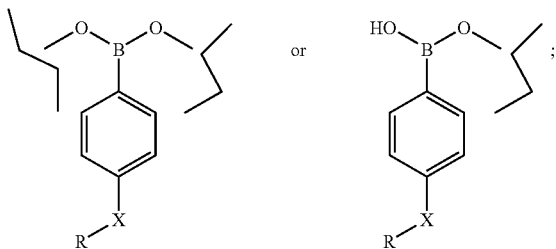

wherein:
X is an electron withdrawing group;
R is a substituted or unsubstituted straight chained hydrocarbyl group optionally containing one or more ether, thioether, phenylene, amine or ammonium linkage; and the Phenyl Ring is substituted or unsubstituted.

58. The method of claim 57 wherein X is —CHD-, —CD$_2$-, —CO—, —CONH—, —COO—, —S(O)—, —S(O$_2$)O— or —SO$_2$—; the Phenyl Ring is optionally substituted with one or more electron withdrawing groups; D is a halogen; and R is a straight chained hydrocarbyl group with an ether or thioether linkage and is substituted at the terminal position with an amine, halogen, —CF$_3$, thiol, ammonium, alcohol, —COOH, —SO$_3$H, —OSO$_3$H or phosphonium group.

59. The method of claim 58 wherein X is —CHD-, —CD$_2$-, —CO—, —CONH—, —COO— or —SO$_2$—.

60. The method of claim 57 wherein X is —CHD-, —CD$_2$-, —COO—, —CONH—, —CO— or —SO$_2$—; the Phenyl Ring is optionally substituted with one or more electron withdrawing groups; D is a halogen; and R is a straight chained hydrocarbyl group with an ether or thioether linkage and is substituted at the terminal position with —[NH—(CH$_2$)$_q$]$_r$—NH$_2$), wherein q is an integer from 2 to about 10 and r is an integer from 1 to about 5, provided that one or more of the secondary amines in —[NH—(CH$_2$)$_q$]$_r$—NH$_2$) are optionally N-alkylated or N,N-dialkylated and the primary amine in —[NH—(CH$_2$)$_q$]$_r$—NH$_2$) is optionally N-alkylated, N,N-dialkylated or N,N,N-trialkylated.

61. A method of treating a subject for obesity, said method comprising the step of administering to the subject an effective amount of a polymer comprising one or more pendent phenyl boronate ester groups represented by a structural formula selected from:

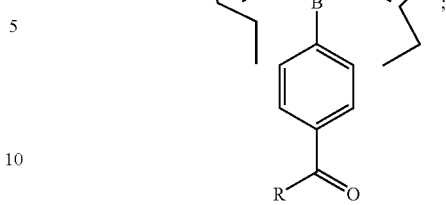

R is a substituted or unsubstituted straight chained hydrocarbyl group optionally containing one or more ether, thioether, phenylene, amine or ammonium linkage; and the Phenyl Ring is substituted or unsubstituted; or a pharmaceutically acceptable salt of said polymer.

62. The method of claim 61 wherein the Phenyl Ring is optionally substituted with one or more additional electron withdrawing groups; R is a straight chained hydrocarbyl group optionally comprising an ether or thioether linkage; and R is substituted at the terminal position with an amine, halogen, —CF$_3$, thiol, ammonium group, alcohol, —COOH, —SO$_3$H, —OSO$_3$H or phosphonium group.

63. The method of claim 62 wherein R is a straight chained hydrocarbyl group comprising an ether or thioether linkage and substituted at the terminal position with an ammonium group.

64. The method of claim 62 wherein R is a straight chained hydrocarbyl group comprising an ether or thioether linkage and substituted at the terminal position with a trialkyl ammonium group.

65. The method of claim 62 wherein R is a straight chained hydrocarbyl group comprising an ether or thioether linkage and substituted at the terminal position with a trimethyl ammonium group.

66. The method of claim 61 wherein the Phenyl Ring is optionally substituted with one or more additional electron withdrawing groups; R is a straight chained hydrocarbyl group with an ammonium linkage and optionally substituted at the terminal position with an amine, halogen, —CF$_3$, thiol, ammonium group, alcohol, —COOH, —SO$_3$H, —OSO$_3$H or phosphonium group.

67. The method of claim 61 wherein the Phenyl Ring is optionally substituted with one or more additional electron withdrawing groups; R is a straight chained hydrocarbyl group with an ammonium linkage.

68. The method of claim 61 wherein the Phenyl Ring is optionally substituted with one or more additional electron withdrawing groups; R is a straight chained hydrocarbyl group substituted at the terminal position with an amine, halogen, —CF$_3$, thiol, ammonium group, alcohol, —COOH, —SO$_3$H, —OSO$_3$H or phosphonium group.

69. The method of claim 68 wherein R is a straight chained hydrocarbyl group substituted at the terminal position with an ammonium group.

70. The method of claim 68 wherein R is a straight chained hydrocarbyl group substituted at the terminal position with a trialkyl ammonium group.

71. The method of claim 57 wherein —XR is —C(O)CH$_2$—O[—(CH$_2$)pO]m-(CH$_2$)p-Y or —C(O)CH$_2$—S[—(CH$_2$)pO]m-(CH$_2$)p-Y, p is 2 or 3, m is an integer from 1–5 and Y is an ammonium group.

72. The method of claim 61 wherein the phenyl boronate ester groups are represented by the following structural formula:

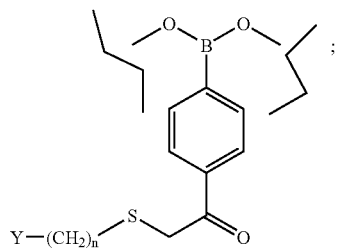

wherein Y is an ammonium group and n is an integer from about 3 to about 30.

73. The method of claim 72 wherein Y is a trialkylammonium group.

74. The method of claim 73 wherein Y a trimethylammonium group.

75. The method of claim 61 wherein the phenyl boronate group is connected directly to the polymer backbone.

76. The method of claim 75 wherein the polymer is polyvinyl alcohol or a polysaccharide.

77. The method of claim 61 wherein the polymer is a fat-binding polymer.

78. The method of claim 77 wherein the polymer is cationic.

79. The method of claim 77 wherein the polymer is a synthetic polyamine.

80. A method of treating a subject for obesity, said method comprising the step of administering to the subject an effective amount of a polymer comprising phenyl boronate functionalized repeat unit, said repeat unit comprising a moiety W represented by a structural formula selected from:

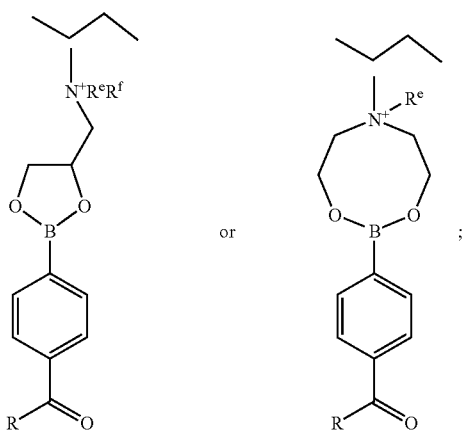

$R^e$ and $R^f$ are independently —H, a substituted or unsubstituted alkyl group or a substituted or unsubstituted benzyl group;

R is a substituted or unsubstituted straight chained hydrocarbyl group optionally containing one or more ether, thioether, phenylene, amine or ammonium linkages; and the Phenyl Ring is substituted or unsubstituted, and pharmaceutically acceptable salts of said polymer.

81. A method of treating a subject for obesity, said method comprising the step of administering to the subject an effective amount of a polymer comprising phenyl boronate functionalized repeat unit, said repeat unit comprising a moiety W represented by a structural formula selected from:

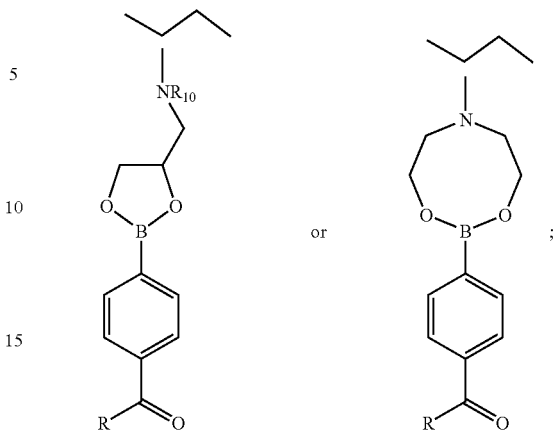

$R_{10}$ is —H, an alkyl group or a benzyl group;

R is a substituted or unsubstituted straight chained hydrocarbyl group optionally containing one or more ether, thioether, phenylene, amine or ammonium linkages; and the Phenyl Ring is substituted or unsubstituted, or a pharmaceutically acceptable salt of said polymer.

82. The method of claim 81 wherein $R_{10}$ is —H.

83. The method of claim 82 wherein the Phenyl Ring is optionally substituted with one or more additional electron withdrawing groups and R is a straight chained hydrocarbyl group comprising an ether or thioether linkage and substituted at the terminal position with an amine, halogen, —$CF_3$, thiol, ammonium group, alcohol, —COOH, —$SO_3H$, —$OSO_3H$ or phosphonium group.

84. The method of claim 83 wherein R is a straight chained hydrocarbyl group comprising an ether or thioether linkage and substituted at the terminal position with an ammonium group.

85. The method of claim 83 wherein R is a straight chained hydrocarbyl group comprising an ether or thioether linkage and substituted at the terminal position with a trialkylammonium group.

86. The method of claim 83 wherein R is a straight chained hydrocarbyl group comprising an ether or thioether linkage and substituted at the terminal position with a trimethylammonium group.

87. The method of claim 82 wherein R is a straight chained hydrocarbyl group comprising an ammonium linkage.

88. The method of claim 82 wherein the boron functionalized repeat unit is represented by the following structural formula:

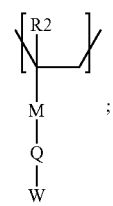

wherein:

M is —CH$_2$—, 1,4-phenylene, —C(O)O—, —C(O)NR1, —C(O)—, —O—, —NR1-, —CH$_2$NR1-, —CH$_2$O—, —N$^+$R1R1- or —CH$_2$N$^+$R1R1-;

Q is an inert spacer group;

R1 is —H, an aliphatic group or a substituted aliphatic group; and

R2 is —H or a C1–C6 alkyl group.

89. The method of claim 88 wherein M is —CH$_2$—, 1,4-phenylene, —C(O)O—, —C(O)NR1, —C(O)—, —O—, —NR1-, —CH$_2$NR1- or —CH$_2$O—.

90. The method of claim 88 wherein the repeat unit is represented by the following structural formula:

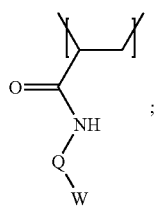

wherein Q is a hydrocarbyl group optionally containing a linking heteroatom functional group.

91. The method of claim 90 wherein Q is a C1 to C30 alkylene group.

92. The method of claim 91 wherein R is —CH$_2$—S—(CH$_2$)n-Y, n is an integer from about 6 to about 30 and Y is an ammonium group.

93. The method of claim 92 wherein Y is a trialkylammonium group.

94. The method of claim 92 wherein Y is a trimethylammonium group.

95. The method of claim 57 wherein the polymer is crosslinked.

96. The method of claim 57 wherein the polymer comprises hydrophobic groups.

97. The method of claim 57 wherein the polymer is a copolymer comprising a hydrophobic comonomer.

98. A method of treating a subject for obesity, said method comprising the step of administering to the subject an effective amount of a polymer comprising repeat units represented by the following structural formula:

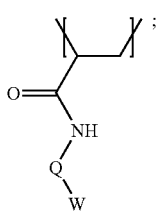

wherein Q is a C1 to C15 alkylene group and W is represented by the following structural formula:

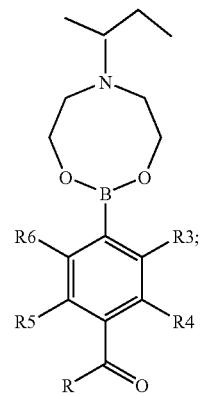

wherein R3–R6 are independently —H or —F, R is —CH$_2$—S—(CH$_2$)n-Y; Y is an ammonium group; and n is an integer from about 6 to about 30; or a pharmaceutically acceptable salt of said polymer.

99. The method of claim 98 wherein Y is a trialkylammonium group.

100. The method of claim 98 wherein Y is a trimethylammonium group.

101. The method of claim 99 wherein R3 R4 and R5 are —H and R4 is —F.

102. The polymer of claim 3, wherein the polymer comprises repeat units characterized by the following structural formula:

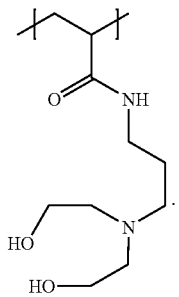

103. A polymer comprising one or more pendent groups represented by a structural formula selected from:

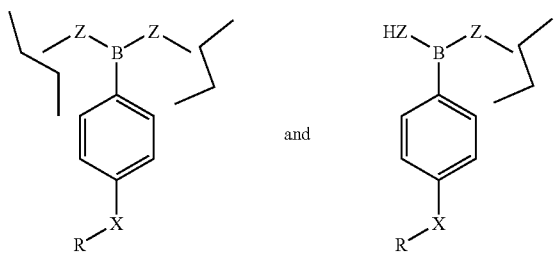

and wherein:
X is an electron-withdrawing group;
each Z is —NH—, —O— or —S— and is independently selected;
R is a substituted or unsubstituted straight chained hydrocarbyl group optionally containing one or more ether, thioether, phenylene, amine or ammonium linkage; and
the Phenyl Ring is substituted.

104. The polymer of claim 103, wherein the phenyl group is further substituted with an electron withdrawing group.

105. A method of inhibiting the uptake of fat in the gastrointestinal tract of a subject in need of such treatment, said method comprising the step of administering to the subject an effective amount of a polymer comprising one or more pendent groups represented by a structural formula selected from:

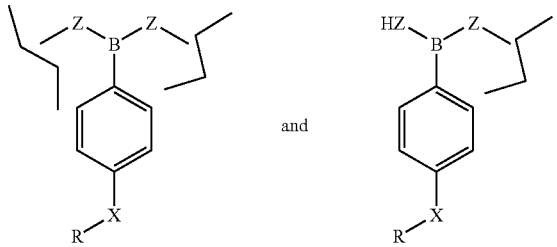

and wherein:
X is an electron-withdrawing group;
each Z is —NH—, —O— or —S— and is independently selected
R is a substituted or unsubstituted straight chained hydrocarbyl group optionally containing one or more ether, thioether, phenylene, amine or ammonium linkage; and
the Phenyl Ring is substituted.

106. A method of treating a subject for obesity, said method comprising the step of administering to the subject an effective amount of a polymer comprising one or more pendent groups represented by a structural formula selected from:

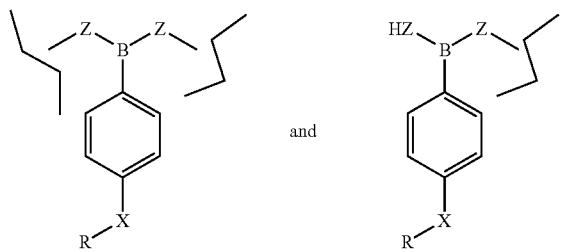

and wherein:
X is an electron-withdrawing group;
each Z is —NH—, —O— or —S— and is independently selected;
R is a substituted or unsubstituted straight chained hydrocarbyl group optionally containing one or more ether, thioether, phenylene, amine or ammonium linkage; and
the Phenyl Ring is substituted.

107. The polymer of claim 2, wherein Ar is substituted with an electron withdrawing group.

108. The method of claim 51, wherein Ar is substituted with an electron withdrawing group.

109. The method of claim 51, wherein Ar is substituted with an electron withdrawing group.

110. The method of claim 61, wherein Ar is substituted with an electron withdrawing group.

111. A method of inhibiting the uptake of fat in the gastrointestinal tract of a subject in need of such treatment, said method comprising the step of administering to the subject an effective amount of the polymer of claim 1.

112. A method of inhibiting the uptake of fat in the gastrointestinal tract of a subject in need of such treatment, said method comprising the step of administering to the subject an effective amount of the polymer of claim 2.

113. A method of inhibiting the uptake of fat in the gastrointestinal tract of a subject in need of such treatment, said method comprising the step of administering to the subject an effective amount of the polymer of claim 3.

114. The polymer of claim 50, wherein n is 11.

115. The polymer of claim 23, wherein n is 11.

116. The polymer of claim 114, wherein the phenyl group is a 3-fluoro-substituted phenyl group.

117. The polymer of claim 115 wherein the phenyl group is a 3-fluoro-substituted phenyl group.

* * * * *

UNITED STATES PATENT AND TRADEMARK OFFICE
CERTIFICATE OF CORRECTION

PATENT NO. : 7,041,280 B2
APPLICATION NO. : 10/187316
DATED : May 9, 2006
INVENTOR(S) : Holmes-Farley et al.

Page 1 of 1

It is certified that error appears in the above-identified patent and that said Letters Patent is hereby corrected as shown below:

In the Claims:
In Claim 1, column 42, line 56, please replace "at least one is" with --at least one Z is.--

In Claim 6, column 43, lines 35-45, replace the following structures:

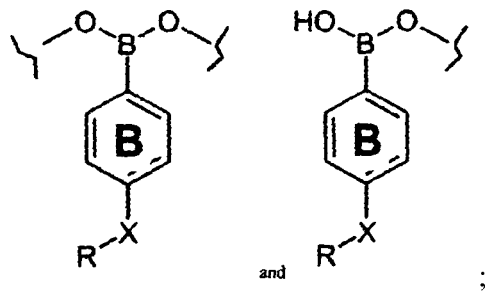

With the following structures:

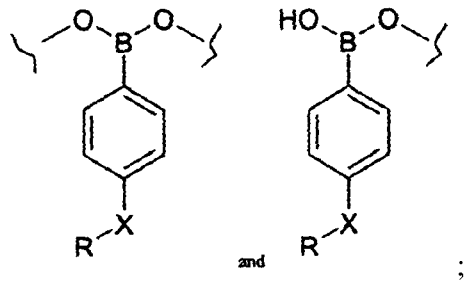

In Claim 109, column 56, line 16, please replace "51" with --54.--

Signed and Sealed this

Tenth Day of October, 2006

JON W. DUDAS
*Director of the United States Patent and Trademark Office*